United States Patent [19]

Shen et al.

[11] 4,038,396
[45] July 26, 1977

[54] ANTI-INFLAMMATORY OXAZOLE[4,5-B]PYRIDINES

[75] Inventors: Tsung-Ying Shen, Westfield; Robert L. Clark, Woodbridge; Arsenio A. Pessolano, Colonia; Bruce E. Witzel, Westfield; Thomas J. Lanza, Edison, all of N.J.

[73] Assignee: Merck & Co., Inc., Rahway, N.J.

[21] Appl. No.: 574,173

[22] Filed: May 2, 1975

Related U.S. Application Data

[63] Continuation-in-part of Ser. No. 552,018, Feb. 24, 1975, abandoned, which is a continuation-in-part of Ser. No. 409,504, Oct. 25, 1973, abandoned, which is a continuation-in-part of Ser. No. 262,898, June 14, 1972, abandoned.

[51] Int. Cl.$^2$ .................... A61K 31/44; C07D 498/04
[52] U.S. Cl. ............................. 424/256; 260/294.8 C; 260/294.9; 260/295 F; 260/296 H
[58] Field of Search ............. 260/294.9, 294.8 C, 260/297 B, 296 H; 424/263, 266, 256

[56] References Cited

PUBLICATIONS

Burger, *Medicinal Chemistry*, Second Edition, Interscience Publishers, p. 497 (1960).
Fraser et al., Chem. Abstracts, vol. 52(6), pp. 4644g–4645c (Mar. 25, 1958).
*Chem. Abstracts*, Sixth Collective Index, Subjects Mi-–Pk, p. 8248 (1961).

*Primary Examiner*—Alan L. Rotman
*Attorney, Agent, or Firm*—Raymond M. Speer; Frank M. Mahon; William H. Nicholson

[57] ABSTRACT

The various isomers of oxazolo- and thiazolopyridines having utility as antiinflammatory, antipyretic and analgesic agents are prepared by condensation of an appropriate amino-hydroxypyridine or amino-mercaptopyridine with a carboxylic acid, halide or anhydride.

36 Claims, No Drawings

ANTI-INFLAMMATORY OXAZOLE[4,5-B]PYRIDINES

This application is a continuation-in-part of copending application Ser. No. 552,018, filed Feb. 24, 1975, now abandoned which in turn is a continuation-in-part of copending application Ser. No. 409,504, filed Oct. 25, 1973, now abandoned, which in turn is a continuation-in-part of Ser. No. 262,898, filed June 14, 1972, now abandoned.

This invention is concerned with oxazolo- and thiazolopyridines and derivatives thereof. More particularly, it is concerned with oxazolo- and thiazolopyridines and derivatives which are antiinflammatory, antipyretic and analgesic agents. The active compounds of this invention include the following isomers:

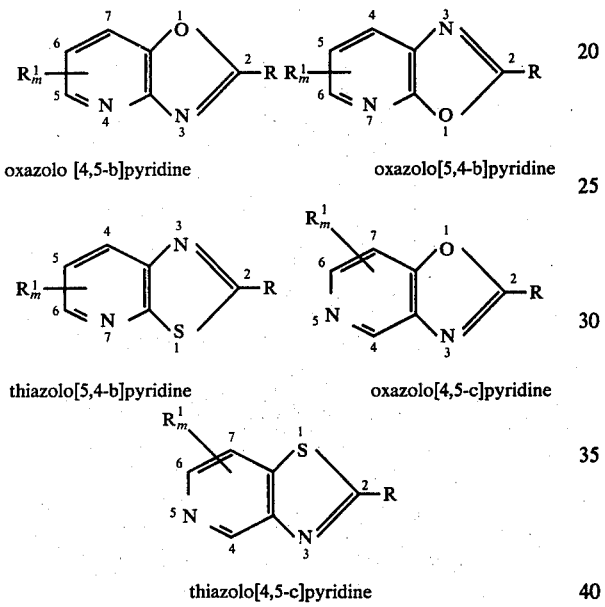

These isomers are depicted by the general formula:

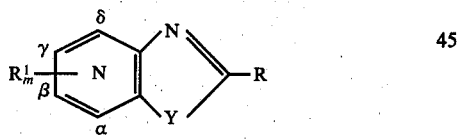

and the quaternary pyridinium salts and N-oxides wherein Y is O or S and the six-membered ring is a pyridine with the nitrogen at one of the $\alpha,\gamma$ or $\delta$ positions of the ring, when Y is O and at the $\alpha$ or $\gamma$ position when Y is S;

R is (a)

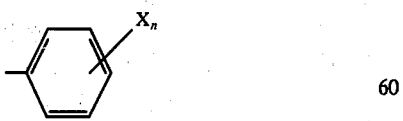

wherein $n$ is an integer from 0-5 and when $n$ is greater than 1, the X substituents may be the same or different and X is 1. halo, such as chloro, fluoro or bromo,
2. lower alkoxy of 1-3 carbon atoms,
3. lower alkyl of 1-5 carbon atoms,
4. nitro,
5. phenyl,
6. lower alkylsulfonyl, wherein the lower alkyl group is of 1-3 carbons,
7. trihalo-lower alkyl, wherein the lower alkyl group is of 1-3 carbon atoms, especially trifluoromethyl,
8. cyano,
9. lower alkylthio, wherein the lower alkyl group is of 1-3 carbon atoms,
10. carbamyl,
11. di(lower alkyl)amino, wherein the lower alkyl groups are the same or different and of 1-3 carbon atoms,
12. lower alkylamino, wherein the lower alkyl group is of 1-3 carbon atoms,
13. lower alkylsulfinyl, wherein the lower alkyl group is of 1-3 carbon atoms,
14. mercapto,
15. trifluoromethoxy,
16. lower alkanoyloxy wherein the lower alkanoyl group is 2-5 carbons,
17. hydroxy,
18. lower alkanoylamino, wherein the lower alkanoyl group is of 2-5 carbons,
19. amino,
20. benzoylamino either unsubstituted or substituted with such as halo, especially chloro or bromo, lower alkyl of 1-3 carbons or lower alkoxy of 1-3 carbons, or
21.

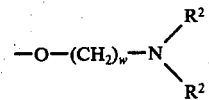

wherein the $R^2$ substitutents are the same or different and represents hydrogen or lower alkyl of 1-3 carbons, and $w$ is an integer from 1 to 3,

22.

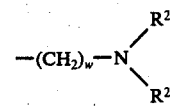

wherein $R^2$ and $w$ are as defined above,

23.

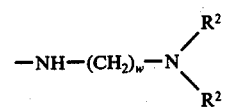

wherein $R^2$ and $w$ are as defined above,

24.

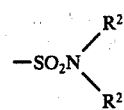

wherein $R^2$ is a defined above,
25. -COOR$^2$ is as defined above,
26. -(CH$_2$)$_w$COOR$^2$ wherein R$^2$ and $w$ are as defined above, 27. -(CH$_2$)$_w$CN wherein $w$ is as defined above,
28. two X radicals on adjacent carbons can be linked together to form a methylenedioxy group; or b.

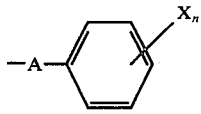

wherein
$x$ and $n$ are as defined above and
A is
1. lower alkyl of 1-3 carbons, preferably 1 carbon,
2. lower alkenyl of 2 to 5 carbons, preferably 2 carbons, or
3. carbonyl;
c. lower alkyl of 1 to 5 carbon atoms such as methyl, ethyl, propyl, butyl or pentyl;
d. lower cycloalkyl of 3 to 7 carbon atoms such as cyclopropyl, cyclobutyl, cyclopentyl, cycloheptyl, and especially cyclohexyl;
e. a 5-6 membered heterocycle containing up to 2 heteroactoms selected from O, N and S, such as pyridyl, 2-pyridone-3,4,5 or 6-yl, furyl, imidazolyl, thiazolyl, or pyrazinyl, each either unsubstituted or substituted with cyano or lower alkyl of 1-5 carbons;
f. napthyl; or
g. adamantyl;

R$^1$ is
a. halo, such as fluoro, chloro, or bromo,
b. lower alkyl of 1-5 carbon atoms such as methyl, ethyl, propyl, butyl or pentyl,
c. nitro,
d. trihalo-lower alkyl wherein the lower alkyl group is of 1-3 carbons, especially trifluoromethyl,
e. amino,
f. benzoylamino,
g. lower alkoxy of 1-3 carbon atoms,
h. di(lower alkyl)amino, where the lower alkyl groups are the same or different and are of 1-3 carbon atoms,
i. lower alkylamino, where the lower alkyl group is of 1-3 carbons,
j. phenyl, or
k. lower alkoxy-carbonylamino, wherein the lower alkoxy group is of 1-5 carbon atoms, and
l. cyano;

$m$ is 0-2.

In the novel method of treatment of this invention, the oxazolopyridines are of particular interest as antiinflammatory agents whether employed systemically or topically.

For systemic purposes, the more preferred compounds are the oxazolo[4,5-b] pyridines and oxazolo[5,4-b]-pyridines of formula:

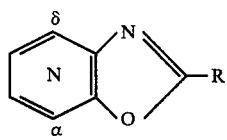

wherein the N is at the $\alpha$ or $\delta$ nuclear position, and wherein R is

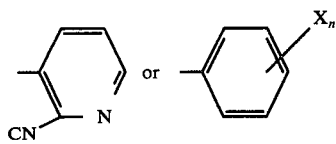

wherein $n$ is 0-3, the X substituents are the same or different and are selected from fluoro, nitro or cyano.

Specific compounds included within the most preferred group of systemically active compounds are:
2-phenyloxazolo[4,5-b] pyridine,
2-(2-fluorophenyl)oxazolo[4,5-b] pyridine,
2-(2-cyanophenyl)oxazolo[4,5-b] pyridine,
2-(2,6-difluorophenyl)oxazolo[4,5-b] pyridine,
2-phenyloxazolo[5,4-b] pyridine,
2-(2-fluorophenyl)oxazolo[5,4-b] pyridine,
2-(2,6-difluorphenyl)oxazolo[5,4-b] pyridine,
2-(2-nitrophenyl)oxazolo[5,4-b] pyridine,
2-(2-cyanophenyl)oxazolo[5,4-b] pyridine, and
2-(2-cyanopyrid-3-yl)oxazolo[5,4-b] pyridine.

For the topical treatment of dermatoses, especially the prophylacetic or therapeutic treatment of ultraviolet erythema, the more preferred compounds are the oxazolo[4,5-b] pyridines, or structure:

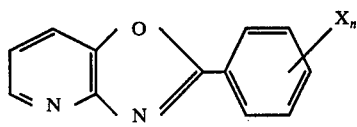

wherein $n$ is 1-3, the X substituents are the same or different and are selected from chloro, lower alkyl, lower alkoxy, or trifluoromethyl.

Specific compounds included within the most preferred group of topically active compounds are:
2-(3-t-butylphenyl)oxazolo[4,5-b] pyridine,
2-[3,5-di (t-butyl)phenyl] oxazolo[4,5-b] pyrinidine,
2-(2-methyl-3-chlorophenyl)oxazolo[4,5-b] pyridine,
2-(2-methyl-3-methoxyphenyl)oxazolo[4,5-b] pyridine,
2-(3-methyl-5-t-butylphenyl)oxazolo[4,5-b] pyridine.

Another embodiment of this invention are the novel compounds found active in the novel method of treatment.

One group of the novel compounds are oxazolo pyridines represented by the structural formula:

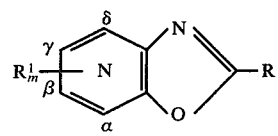

wherein the six-membered ring is a pyridine with the nitrogen at the $\alpha$ or $\delta$ position, especially the $\delta$ position, and the quaternary salts and N-oxides thereof, wherein R is

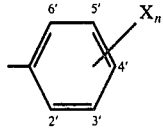

wherein n is an integer from 1-5, and when n is greater than 1, and X substituents may be the same or different; and
X is
1. halo,
2. lower alkyl of 1-5 carbon atoms,
3. nitro,
4. lower alkoxy of 1-3 carbon atoms,
5. phenyl,
6. lower alkylsulfonyl, wherein the lower alkyl group is of 1-3 carbon atoms,
7. trihalo-lower alkyl, wherein the lower alkyl group is of 1-4 carbon atoms, especially trifluoromethyl,
8. cyano,
9. lower alkylthio, wherein the lower alkyl group is of 1-3 carbon atoms,
10. carbamyl,
11. di(lower alkyl)amino, wherein the lower alkyl groups are the same or different and of 1-3 carbon atoms,
12. lower alkylamino, wherein the lower alkyl group is of 1-3 carbon atoms,
13. lower alkylsulfinyl, wherein the lower alkyl group is of 1-3 carbon atoms,
14. mercapto,
15. trifluoromethoxy,
16. lower alkanoyloxy wherein the lower alkanoyl group is 2-5 carbons,
17. hydroxy,
18. lower alkanoylamino, wherein the lower alkanoyl group is of 2-5 carbons,
19. amino,
20. benzoylamino either unsubstituted or substituted with such as halo, especially chloro or bromo, lower alkyl of 1-3 carbons or lower alkoxy of 1-3 carbons, or
21.

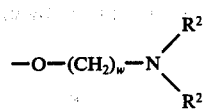

wherein the R² substituents are the same or different and represents hydrogen or lower alkyl of 1-3 carbons, and w is an integer from 1 to 3,
22.

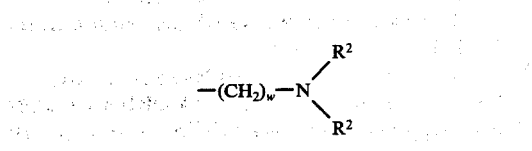

wherein R² and w are as defined above,
23.

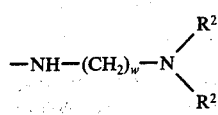

wherein R² and w are as defined above,
24.

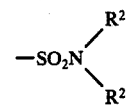

wherein R² is as defined above,
25. —COOR² wherein R² is as defined above,
26. —(CH₂)_wCOOR² wherein R² and w are as defined above,
27. —(CH₂)_wCN wherein w is as defined above,
28. two X radicals on adjacent carbons can be linked together to form a methylenedioxy group; or

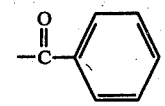

c. lower cycloalkyl of 3 7 carbon atoms such as cyclopropyl, cyclobutyl, cyclopentyl, cycloheptyl, and especially cyclohexyl;
d. a 5-6 membered heterocycle containing up to 2 heteroatoms selected from O, N and S, such as pyridyl, 2-pyridone-3,4,5 or 6-yl, furyl, imidazolyl, thiazolyl, or pyrazinyl, each either unsubstituted or substituted with cyano or lower alkyl of 1-5 carbons;
e. naphthyl; or
f. adamantyl;
R¹ is
a. halo, such as fluoro, chloro or bromo,
b. lower alkyl of 1-5 carbon atoms such as methyl, ethyl, propyl, butyl or pentyl,
c. nitro,
d. trihalo-lower alkyl wherein the lower alkyl group is of 1-3 carbons, especially trifluoromethyl,
e. amino,
f. benzoylamino,
g. lower alkoxy of 1-3 carbon atoms,
h. di(lower alkyl)amino, where the lower alkyl groups are the same or different and are of 1-3 carbon atoms,
i. lower alkylamino, where the lower alkyl group is of 1-3 carbons,
j. phenyl, or
k. lower alkoxy-carbonylamino, wherein the lower alkoxy group is of 1-5 carbon atoms, and
l. cyano;
m is 0-2;
with the proviso that R is not 4-lower alkylphenyl.
A preferred class of such compounds is that wherein R is

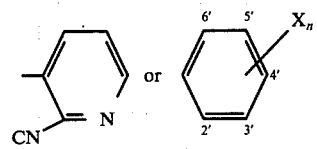

n is 1-3, and X represents halo, trifluoromethyl, lower alkoxy, lower alkyl, nitro or cyano, and m is 0.
A still more preferred class is that wherein R is

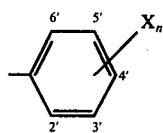

n is 1-3 and X represents
halo, nitro, lower alkoxy, trifluoromethyl, lower alkyl, or cyano, and m is 0.

The most preferred novel compounds within this class are the following:
2-(2-fluorophenyl)oxazolo[4,5-b] pyridine,
2-(2-cyanopyridyl)oxazolo[4,5-b]pyridine,
2-(2,6-difluorophenyl)oxazolo[4,5-b]pyridine,
2-(3,5-dimethylphenyl)oxazolo[4,5-b]pyridine,
2-(2-methyl-3-chlorophenyl)oxazolo[4,5-b]pyridine,
2-(3-methoxyphenyl)oxazolo[4,5-b]pyridine,
2-(2-chloro-3-methylphenyl)oxazolo[4,5-b]pyridine,
2-(2,5-dimethyl-3-chlorophenyl)oxazolo[4,5-b]pyridine
2-(2-fluorophenyl)oxazolo[5,4-b]pyridine,
2-(2,6-difluorophenyl)oxazolo[5,4-b]pyridine,
2-(2-nitrophenyl)oxazolo[5,4-b]pyridine,
2-(2-cyanophenyl)oxazolo[5,4-b]pyridine, and
2-(2-cyanopyrid-3-yl)oxazolo[5,4-b]pyridine.

Another group of the novel compounds is thiazolopyridines represented by the structural formula:

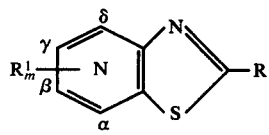

wherein the six-membered ring is a pyridine with the nitrogen at the α or γ position, especially the α-position. R is (a)

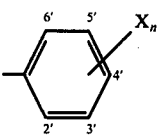

wherein
n is an interger from 1-5 and when n is greater than 1, the X substituents may be the same or different; and X is
1. halo,
2. lower alkoxy of 1-3 carbon atoms,
3. nitro,
4. lower alkyl of 1-5 carbon atoms,
5. phenyl,
6. lower alkylsulfonyl, wherein the lower alkyl group is of 1-3 carbon atoms,
7. trihalo-lower alkyl, wherein the lower alkyl group is of 1-3 carbon atoms, especially trifluoromethyl,
8. cyano,
9. lower alkylthio, wherein the lower alkyl group is of 1-3 carbon atoms,
10. carbamyl,
11. di(lower alkyl)amino, wherein the lower alkyl groups are the same or different and of 1-3 carbon atoms,
12. lower alkylamino, wherein the lower alkyl group is of 1-3 carbon atoms,
13. lower alkylsulfinyl, wherein the lower alkyl group is of 1-3 carbon atoms,
14. mercapto,
15. trifluoromethoxy,
16. lower alkanoyloxy wherein the lower alkanoyl group is 2-5 carbons,
17. hydroxy,
18. lower alkanoylamino, wherein the lower alkanoyl group is of 2-5 carbons,
19. amino,
20. benzoylamino either unsubstituted or substituted with such as halo, especially chloro or bromo, lower alkyl of 1-3 carbons or lower alkoxy of 1-3 carbons, or
21.

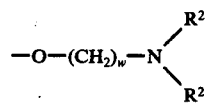

wherein the $R^2$ sustituents are the same or different and represents hydrogen or lower alkyl of 1-3 carbons, and w is an integer from 1 to 3,
22.

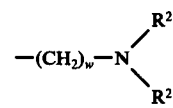

wherein $R^2$ and w are as defined above,
23.

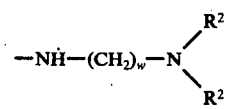

wherein $R^2$ and w are as defined above,
24.

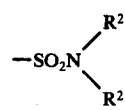

wherein $R^2$ is as defined above,
25. —COOR$^2$ wherein $R^2$ is as defined above,
26. —(CH$_2$)wCOOR$^2$ wherein $R^2$ and w are as defined above,
27. -(CH$_2$)$_w$CH wherein w is as defined above,
28. two X radicals on adjacent carbons can be linked together to form a methylenedioxy group; or b.

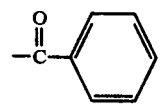

c. lower cycloalkyl of 3 to 7 carbon atoms such as cyclopropyl, cyclobutyl, cyclopentyl, cycloheptyl, and especially cyclohexyl;
d. a 5-6 membered heterocycle containing up to 2 heteroatoms selected from O, N and S, such as pyridyl, 2-pyridone-3,4,5 or 6-yl, furyl, imidazolyl, thiazolyl, or pyrazinyl, each either unsubstituted or substituted with cyano or lower alkyl of 1-5 carbons;
e. naphthyl; or
f. adamantyl;
$R^1$ is
a. halo, such as fluoro, chloro or bromo,
b. lower alkyl of 1-5 carbon atoms such as methyl, ethyl, propyl, butyl or pentyl,
c. nitro,
d. trihalo-lower alkyl wherein the lower alkyl group is of 1-3 carbons, especially trifluoromethyl,
e. amino,
f. benzoylamino,
g. lower alkoxy of 1-3 carbon atoms,
h. di(lower alkyl) amino, where the lower alkyl groups are the same or different and are of 1-3 carbon atoms,
i. lower alkylamino, where the lower alkyl group is of 1-3 carbons,
j. phenyl, or
k. lower alkoxy-carbonylamino, wherein the lower alkoxy group is of 1-5 carbon atoms, and
l. cyano;
$m$ is 0-2;
with the proviso that R is not 4-aminophenyl or 4-nitrophenyl.

A preferred class of such compounds is that in which R is

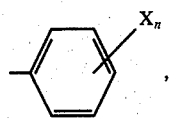

$n$ is 1 or 2, and X represents lower alkyl, lower alkoxy, halo, nitro or cyano, and $m$ is zero.

This invention also includes methods of treating inflammation in its varying manifestations, utilizing antiinflammatory compositions containing oxazolo (or thiazolo) pyridines. In addition, these compositions exhibit potent analgesic and antipyretic activity and, therefore, this invention also relates to analgesic and antipyretic methods and compositions. Furthermore, this invention is concerned with analgesic and antipyretic methods for the relief and treatment of pain and fever not symptomatically related to an inflammatory condition.

Following the discovery of the now well-known antiinflammatory properties of the steroids and the equally well known undesirable side-effects of steroid therapy there was an intensive search made for non-steroid antiinflammatory agents. The search was productive in the discovery of a few highly effective, useful, non-steroidal agents each with its own undesirable side-effects and contraindications.

Now, with the present invention there is available a new series of compounds highly effective as antiinflammatory, antipyretic and analgesic agents. Like the other known potent antiinflammatory agents, the compounds of this invention are inhibitors of prostaglandin E synsthesis.

The oxazolo (and thiazolo) pyridines of the invention possess antiinflammatory, analgesic and antipyretic activity. They are of value in the treatment of arthritic and dermatological disorders or like conditions responsive to antiinflammatory drugs. In general they are indicated for a wide variety of conditions where one or more of the symptoms of inflammation, fever and pain are manifested. Included within this category are diseases such as rheumatoid arthritis, osteoarthritis, gout, infectious arthritis, rheumatic fever, ultraviolet erythema, atopic dermatitis, contact determatitis, seborrheic dermatitis, diaper rash, and inflammatory conditions of the ocular system. As indicated above, the compounds utilized in the practice of the invention also possess a useful degree of analgesic and antipyretic activity.

For these purposes of compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intraveneous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in the form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, steric acid or talc. The tablets may be uncoated or they may be coated by known techniques to delay distinegration and absorption in the gastrointestinal tract and thereby provide a sustained action over a longer period. For example, a time delay material such as glyceryl monostearate or glyceryl distearate may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example, peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan mono-oleate. The said aqueous suspensions may also contain one or more preservative, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention may also be administered in the form of suppositories for rectal administration of the drug. These compositions can be prepared by mixing the drug with a suitable non-irritating excipient which is solid at ordinary temperatures but a liquid at the rectal temperatures and will therefore melt in the rectum to release the drug. Such materials are cocoa butter and polyethylene glycols.

Dosage levels of the order of 0.1 mg. to 140 mg. per kilogram of body weight per day are useful in the treatment of the above-indicated conditions. For example, inflammation, pain, and fever are effectively treated by the administration of about 0.5 to 50 mg. of the compound per kilogram of body weight per day. Advantageously, from about 1 mg. to about 15 mg. per kilogram of body weight per daily dosage produces highly effective results.

The amount of active ingredient that may be combined with the carrier materials to produce a single dosage form will vary depending upon the host treated and the particular mode of administration. For example, a formulation intended for the oral administration to humans may contain from 5 mg. to 5 gm. of active agent compounded with an appropriate and convenient amount of carrier material which may vary from about 5 to about 95 percent of the total composition. Dosage units forms will generally contain between from about 25 mg. to about 500 mg. of active ingredient.

For topical use, creams, ointments, jellies, solutions or suspensions containing the antiinflammatory agents are employed. The topical pharmaceutical compositions include about 0.01% to 0.25%, preferably about 0.1% by weight of active compound, in admixture with a suitable vehicle. The vehicle generally comprises water, an organic solvent, and a thickening agent. The water ordinarily constitutes from about 8% to 18% of the gel vehicle, preferably about 13%. The organic solvent ordinarily constitutes about 60% to 90% of the gel vehicle. Representative solvents are ethyl alcohol, isopropyl alcohol, propylene glycol, glycerine, 2-octyl dodecanol and methyl pyrrolidine, and preferably isopropyl alcohol; propylene glycol mixtures at a ratio of 0.5 to 0.6 parts isopropyl alcohol to 1.0 part propylene glycol. The solubility of the oxazolopyridine in the solvent system selected should be such as to obtain maximum partitioning of the active compound from the vehicle to the skin. The thickening agent, preferably hydroxyethyl cellulose, hydroxypropyl cellulose, and the like, ordinarily constitutes from 0.5 to 4.0% of the gel vehicle. Optionally, a stabilizing agent, such as disodium edetate, sodium citrate, dipotassium edetate, citric acid, and the like, in the proportion of about 0.02% to 0.1% of the gel vehicle may be employed, if desired.

A preferred topical pharmaceutical composition is prepared as follows: about 2.60 g. of hydroxypropyl cellulose is added to a solution of 0.05 g. of disodium edetate in 13.00 g. purified water while agitating the mixture and maintaining the temperature at about 60° C., and the agitation is continued until the hydroxypropyl cellulose is completely dispersed and wetted. To the resulting dispersed mixture is added, with agitation, a solution containing 0.1 g. of, for example, 2-(2-methyl-3-chlorophenyl)oxazolo[4,5-b]pyridine dispersed in a mixture of 30.00 g. of anhydrous isopropyl alcohol and 54.25 g. of propylene glycol. The resulting gel mixture is stirred vigorously at room temperature for a period of approximately 15 minutes thereby forming a pharmaceutical composition adapted for the treatment of topical antiinflammatory conditions.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of this invention are generally prepared by condensation cyclization of an amino-hydroxypyridine with a carboxylic acid, acid anhydride, or acid halide, of formula

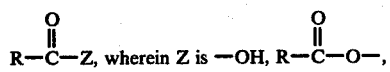

R—C—Z, wherein Z is —OH, R—C—O—, or halide according the the equation:

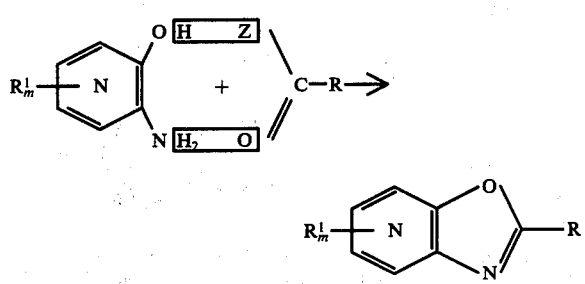

Depending on the condensing agent employed and to some extent the particular amino-hydroxy-pyridine employed, the reaction can appear as either a concerted one-step ring closure or a two-step process comprising as the first step, the formation of an amide followed by ring closure of the amide to form the oxazolo ring. In many instances it is found advisable and convenient to isolate the intermediate amide and ring close in a second discrete step.

The oxazolopyridines in general can be prepared by condensation of an amino hydroxypyridine with an acid anhydride either with or without the influence of a condensing agent such as polyphosphoric acid or polpyphosphoric ester. In either case the amino hydroxypyridine is mixed with 1 to about 3 molar equivalents of the acid or ester, is heated to reflux temperature for about 5 to about 30 minutes. After some cooling the excess polyphosphoric acid and anhydride are decomposed and the product is isolated by standard techniques.

The isomeric oxazolopyridine can also be prepared by condensation of the appropriate amino hydroxypyridine with a carboxylic acid under the influence of polyphosphoric acid or polyphosphoric ester. A mixture of the pyridine and a slight excess of a carboxylic acid, in the presence of polyphosphoric acid or ester, is heated for about 5 minutes to about one hour at a temperature of from 100° C. to about 300° C., preferable between about 130° C. and 230° C. The polyphosphoric acid or ester is decomposed with water and the desired product is obtained by making the solution alkaline.

All of the oxazolopyridine isomers may be prepared via an intermediate amide by reacting an acid halide with the appropriate amino-hydroxy-pyridine preferably in approximately equimolar amounts in the presence of an acid acceptor. Any of the common acid acceptors normally employed in N-acylations can be used, but it is found convenient to use an organic base such as pyridine, triethylamine or an equivalent base. Sufficient organic base can be employed to act also as the solvent, or another inert organic solvent such as dimethylformamide, benzene, dioxane, glyme or diglyme or the like, can be used as a medium for the reaction. The amide produced by the above reaction is then ring-closed to an oxazolopyridine by refluxing a mixture of it and a condensing agent such as phosphorus oxychloride for from 1 to about 20 hours, or by heating the amide with polyphosphoric acid at about 100° C. to about 300° C., preferably at about 130° C. to about 230° C for 5 to about 60 minutes. Other condensing agents usable in place of phosphorus oxychloride are phosphorus pentoxide, phosphorus oxybromide, thionyl chloride, and phosphorus tribromide.

The isomeric thiazolo[5,4-b] and [4,5-b]pyridines are prepared by treating the appropriate intermediate amides described above with phosphorus pentasulfide. The amide is dissolved in a mixture of a high boiling inert solvent such as toluene, xylene or the like, and an organic base such as pyridine or triethylamine, heated to reflux, treated with an excess of phosphorus pentasulfide and refluxed for from about 10 to about 24 hours.

The thiazolo[4,5-b]pyrdines are prepared by condensation of a carboxylic acid anhydride with the appropriate mercapto-3-aminopyridine. The reaction is readily conducted by heating a mixture of the two components at a temperature above the fusion point of the mixture and up to its reflux temperature.

The N-oxides of the oxazolo and thiazolopyridines are prepared by warming at 50° C. to about 100° C., a solution of the oxazolo- or thiazolopyridine in acetic acid with hydrogen peroxide.

The N-lower alkyl pyridinium iodides are prepared by refluxing a solution of the oxazolo- or thiazolopyridine in acetone, with a lower alkyl iodide.

The following examples describe the preparation of specific compounds of this invention and are meant to be illustrative only and not limiting to the scope of this invention.

EXAMPLE 1

2-Phenyloxazolo [4,5-b]pyridine

A mixture of 21 g. of 2-amino-3-hydroxypyridine and 130 g. of benzoic anhydride was heated to a melt, then heated more until the mixture was refluxing. After ten minutes the heat was removed and after several minutes cooling the melt was poured into 2-liters of benzene. This solution was extracted with 4 × 200 ml. of 2.5 N hydrochloric acid. This acidic solution was then made basic with sodium hydroxide solution. The precipitate was collected and recrystallized from 90 ml. of absolute ethanol to yield 12.5 g. of 2-phenyloxazolo[4,5-b]pyridine, m.p. 125°–127° C.

Employing substantially the procedure of Example 1 but substituting for the benzoic anhydride used therein an equivalent amount of an anhydride of formula (R-CO)$_2$O there is produced the 2-R-oxazolo[4,5-b]pyridines depicted in Table I in accordance with the following equation:

TABLE I

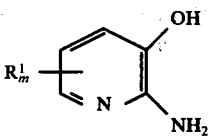

| Example | R¹ | R | m.p. (° C.) |
|---|---|---|---|
| 2 | H | 4-chlorophenyl | 165–166 |
| 3 | H | 4-methoxyphenyl | 176–177 |
| 4 | H | 4-fluorophenyl | 146 |
| 5 | H | 3-pyridyl | 155–156 |

EXAMPLE 6

2-(2-Fluorophenyl)oxazolo[4,5-b]pyridine

A mixture of 3.3 g. (0.03 mole) of 2-amino-3-hydroxypyridine, 5.6 g. (0.04 mole) of 2-fluorobenzoic acid, and 12 g. of polyphosphoric acid was heated to 175° C. and held there for 10 minutes. After cooling a little, the melt was poured into a mixture of ice and water. After stirring to decompose the polyphosphoric acid, the mixture was made alkaline with ammonium hydroxide solution. The resulting precipitate was collected and recrystallized from benzene-petroleum ether to give 4.0 g. of 2-(2-fluorophenyl)oxazolo[4,5-b]pyridine, m.p. 126°–127° C.

Using the procedure of Example 6, byt substituting for the 2-fluorobenzoic acid and the 2-amino-3-hydroxypyridine employed therein, equimolar amounts of a benzoic acid of formula R-COOH, and a 2-amino-3-hydroxypyridine of formula:

respectively, there are produced the 2-R-oxazolo[4,5-b]pyridines depicted in Table II in accordance with the following equation:

Table II

| Example | Reaction Temp. (0° C.) | R' | R | m.p. (° C.) |
|---|---|---|---|---|
| 6(a) | 180 | H | 2,4-dimethylphenyl | 93–95 |
| 6(b) | 180 | H | 2,5-dimethylphenyl | 86–87 |
| 6(c) | 180 | H | 3,4-dimethylphenyl | 145–148 |
| 6(d) | 185 | H | 2-fluoro-5-methylphenyl | 126.5–130 |
| 6(e) | 180 | H | 3-ethylphenyl | 79–81 |
| 6(f) | 200 | H | 2-bromo-4-methylphenyl | 145–147 |
| 6(g) | 180 | H | 2-bromo-5-nitrophenyl | 195–198 |
| 6(h) | 180 | H | 3-t-butyl-5-methylphenyl | 131–132 |
| 6(i) | 150 | H | 2-methyl-3-methoxyphenyl | 138–141 |
| 6(j) | 175 | 6-CH₃ | 2-methyl-3-chlorophenyl | 139–143 |
| 6(k) | 180 | H | 3-iodophenyl | 172–176 |
| 6(l) | 165 | H | 2-chloro-3-mthoxyphenyl | 165.5–167 |
| 6(m) | 180 | H | 3-fluoro-2-methylphenyl | |
| 6(n) | 180 | H | 3-chloro-5-methylphenyl | |
| 6(o) | 180 | H | 3-methyl-5-methoxyphenyl | |
| 6(p) | 180 | H | 2-methyl-3-trifluoromethylphenyl | |
| 6(q) | 180 | H | 2-chloro-3-ethyl phenyl | |
| 6(r) | 180 | H | 3-4-butyl(phenyl | 124–126 |
| 7 | 210 | H | β-naphthyl | 160–161 |
| 8 | 190 | H | 5-n-propylpyrid-2-on-3-yl | 251–252 |
| 9 | 185 | H | 2,4-difluorophenyl | 140–142 |
| 10 | 190 | H | 2-ethylphenyl | 150 (dec.) |
| 11 | 230 | H | 2,6-dichlorophenyl | 139–140 |
| 12 | 210 | H | 2-chloro-6-fluorophenyl | 86–88 |
| 13 | 210 | H | 3-chlorophenyl | 142–143 |
| 14 | 220 | H | 2-chlorophenyl | 92–93 |
| 15 | 140–145 | H | 3,4-dimethoxyphenyl | 193–195 |
| 16 | 200 | H | styryl | 109–110 |
| 17 | 200 | H | 3-nitrophenyl | 199–201 |
| 18 | 155 | H | 3-methoxyphenyl | 111–113 |
| 19 | 200 | H | biphenyl | 188–189 |
| 20 | 155 | H | 2-methoxyphenyl | 108–109 |
| 21 | 155 | H | 2-methylphenyl | 64–66 |
| 22 | 145 | H | benzyl | 95–97 |
| 23 | 130 | H | 4-chloro-2-fluorophenyl | 154–156 |
| 24 | 160 | H | 2,5-difluorophenyl | 130–132 |
| 25 | 150–180 | H | 2,5-dichlorophenyl | 119–120 |
| 26 | 170 | H | cyclohexyl | 95–96 |
| 27 | 175 | H | 2-bromophenyl | 60–61 |
| 28 | 210 | H | 4-methylsulfonyl- | 277–279 |

Table II-continued $$R^1_m \overset{OH}{\underset{N}{\bigcirc}} \underset{NH_2}{} + R\text{—COOH} \longrightarrow R^1_m \overset{O}{\underset{N}{\bigcirc}} \underset{N}{\bigcirc}\text{—}R$$

| Example | Reaction Temp. (0° C.) | R' | R | m.p. (° C.) |
|---|---|---|---|---|
| 29 | 175 | H | phenyl pyrid-2-yl | 197–198 |
| 30 | 210 | H | pyrid-4-yl | 171–173 |
| 31 | 210 | H | 2,6-difluorophenyl | 113–114 |
| 32 | 220 | H | 2-fluorobenzyl | 80–82 |
| 33 | 160 | H | 2-trifluoromethyl-phenyl | 63–64 |
| 34 | 180–205 | H | 2-methylsulfonyl-phenyl | 140–144 |
| 35 | 180–185 | H | thiazol-4-yl | 215–216 |
| 36 | 180–185 | H | 3-hydroxyphenyl | 209–210 |
| 37 | 180–185 | H | 3-ethoxyphenyl | 102–104 |
| 38 | 180–185 | H | 2-methylthiophenyl | 135.5–137.5 |
| 39 | 180–185 | H | 3-methylphenyl | 106–107.5 |
| 40 | 225 | H | imidazol-4(or 5)-yl | 271–272 |
| 41 | 180–185 | H | 3,5-dimethoxyphenyl | 151–152.5 |
| 42 | 180–185 | H | 2-fluoro-3-methoxy-phenyl | |
| 43 | 180–185 | H | 2-fluoro-5-methoxy-phenyl | |
| 44 | 180–185 | H | 3-di(methyl)aminophenyl | |
| 45 | 180–185 | H | 3-methylaminophenyl | |
| 46 | 180–185 | H | 3-trifluoromethyl-phenyl | |
| 47 | 180–185 | H | 3-methylthiophenyl | 82–84 |
| 48 | 180–185 | H | 3-mercaptophenyl | |
| 49 | 180–185 | H | 2-mercaptophenyl | |
| 50 | 180–185 | H | 4-mercaptophenyl | |
| 51 | 180–185 | H | 2,3-dimethylphenyl | 72–73 |
| 52 | 180–185 | H | 2,3-dimethoxyphenyl | |
| 53 | 180–185 | H | 4-trifluoromethoxy-phenyl | 139–141 |
| 54 | 180–185 | H | 3,4-methylenedioxy-phenyl | |
| 55 | 180–185 | H | adamantan-1-yl | |
| 55(a) | 180–185 | H | 2-dimethylsulfamoyl-phenyl | |
| 55(b) | 180–185 | H | 3-dimethylsulfamoyl-phenyl | |
| 55(c) | 180–185 | H | 4-dimethylsulfamoyl-phenyl | |

EXAMPLE 56

2-(4-Tolyl)oxazolo[4,5-b]pyridine

Step A: Preparation of 3-hydroxy-2-(4-toluylamino)-pyridine

To a solution of 5.5 g. (0.05 mole) of 2-amino-3-hydroxy pyridine in 150 ml. of dimethylformamide and 11 ml. of triethylamine was added portionwise 9.3 g. (0.06 mole) of 4-toluyl chloride with slight cooling and the mixture was stirred at ambient temperature overnight. The resulting precipitate was removed by filtration. The filtrate was evaporated to dryness and the resulting oil was crystallized from ether and recrystallized from aqueous ethanol to give 3.1 g. of 3-hydroxy-2-(4-toluylamino)pyridine, m.p. 134°–135° C.

Step B: Preparation of 2-(4-tolyl)oxazolo[4,5-b]pyridine

A solution of 500 mg. of 3-hydroxy-2-(4-toluylamino)pyridine in 4 ml. of phosphorus oxychloride was heated on the steam bath for 18 hours. The excess phosphorus oxychloride was evaporated and the residue was treated with ice-water. The mixture was clarified by filtration and neutralized with concentrated ammonium hydroxide. The resulting precipitate was collected, washed with water, dried and recrystallized from benzene-petroleum ether to give 200 mg. of 2-(4-tolyl)oxazolo[4,5-b]pyridine, m.p. 135°–136° C.

EXAMPLE 57

2-(2-Fluorophenyl)oxazolo[4,5-b]pyridine-4-oxide

A solution of 1 g. of 2-(2-fluorophenyl)oxazolo-[4,5-b]pyridine (from Example 6) in 10 ml. of acetic acid was treated with 2 ml. of 30% hydrogen peroxide and heated on the steam bath for 16 hours. After cooling the mixture was diluted with ice-water. The precipitate was collected and recrystallized from dioxane-ether to give 2-(2-fluorophenyl)oxazolo [4,5-b]pyridine-4-oxide, m.p. 214°–216° C.

EXAMPLE 58

N-Methyl 2-(2-fluorophenyl)oxazolo [4,5-b]pyridinium iodide

A solution of 600 mg. of 2-(2-fluorophenyl)-oxazolo [4,5-b]pyridine and 10 ml. of methyliodide in 75 ml. of acetone was refluxed for 3 hours. The solution was concentrated to dryness and the residue was extracted with ether. The ether-insoluble material was recrystallized from methanol-ethyl acetate to give 500 mg. of N-methyl 2-(2-fluorophenyl)oxazolo [4,5-b]pyridinium iodide, m.p. 229° C.

EXAMPLE 59

2-Ethyloxazolo [4,5-b]pyridine

A mixture of 4.4 g. of 2-amino-3-hydroxypyridine, 10.4 g. of propionic anhydride and 15 g. of polyphosphoric acid was heated at 168° C. for 15 minutes. The reaction mixture was cooled slightly and poured into ice water and stirred until the polyphosphoric acid had decomposed. The solution was made alkaline with solid sodium bicarbonate and extracted with 150 ml. of methylene chloride. The dried methylene chloride solution was concentrated to dryness and the residue was dissolved in ether and filtered through aluminum oxide. From the ether filtrate there was obtained 1.2 g. of 2-ethyloxazolo[4,5-b]pyridine, m.p. 52°–53° C.

EXAMPLE 60

2-[3-Di (methyl)aminophenyl]oxazolo [4,5-B]pyridine Dihydrochloride

A mixture of 2.4 g. of 2-(3-nitrophenyl) oxazolo-[4,5-b]pyridine, 6 ml. of 37% formaldehyde solution, 50 ml. of acetic acid and 0.25 g. of Raney nickel was hydrogenated. The catalyst was removed by filtration and the filtrate was concentrated to dryness. The residue was distributed between aqueous sodium bicarbonate solution and benzene. The benzene phase was separated, dried over anhydrous sodium sulfate and concentrated to an oil. The oil was taken up in methylene chloride and treated with dry ether saturated with hydrogen chloride. The resulting precipitate was collected and washed with ether to give 2-(3-dimethylaminophenyl) oxazolo-[4,5-b]pyridine·2HCl, m.p. 208°–209° C.

EXAMPLE 61

2-(3-Aminophenyl)oxazolo[4,5-b]pyridine

A mixture of 700mg. of 2-(3-nitrophenyl)oxazolo-[4,5-b]pyridine in 50 ml. of ethanol was hydrogenated over 150 mg. of 5% palladium-on-carbon catalyst. The catalyst was removed by filtration and the solvent was concentrated to dryness. The residue was recrystallized from chloroformpetroleum ether to give 2-(3-aminophenyl)oxazolo[4,5-b]pyridine, m.p. 179°–180.5° C.

EXAMPLE 62

2-Benzoyloxazolo[4,5-b]pyridine

A mixture of 800 mg. of 2-benzyloxazolo [4,5-b]pyridine, 2.5 g. of potassium permanganate, 35 ml. of water and 6 drops of 2.5 N sodium hydroxide solution was heated at 50°–55° C. for 3 hours. After cooling, sulfuric acid was added to about pH 6 and sufficient sodium bisulfite was added to remove the manganese dioxide. The crystalline precipitate remaining was collected and recrystallized from ethylacetate to give 2-benzoyloxazolo [4,5-b]pyridine, m.p. 151°–153° C.

EXAMPLE 63

5-Methyl-2-phenyloxazolo[4,5-b]pyridine

Step A: Preparation of 3-hydroxy-6-methyl-2-nitropyridine

To 40 ml. of ice cold concentrated sulfuric acid was added 10.9 g. of 3-hydroxy-6-methylpyridine. Maintaining the temperature at 6° C., 4.7 ml. of fuming nitric acid was added dropwise with stirring. The mixture was allowed to warm to room temperature overnight. Ice (200 g.) was added with stirring. After the ice had melted, the precipitate was collected, washed with water and dried to give 3-hydroxy-6-methyl-2-nitropyridine, m.p. 103°–105° C.

Step B: Preparation of 2-amino-3-hydroxy-6-methylpyridine

3-Hydroxy-6-methyl-2-nitropyridine (3.5 g.) in 75 ml. of methanol was reduced over 1 g. of 5% palladium-on-carbon catalyst. The catalyst was removed by filtration and the filtrate was concentrated to dryness to give 2-amino-3-hydroxy-6-methylpyridine which was used directly in the next stop.

Step C: Preparation of 5-methyl-2-phenyloxazolo[4,5-b]pyridine

A mixture of 1.25 g. of 2-amino-3-hydroxy-6-methylpyridine, 6 g. of polyphosphoric acid and 2.0 g. benzoic acid was heated at 190°–200° C. for 10 minutes. The cooled mixture was diluted with water and basified with solid sodium bicarbonate. The resulting precipitate was collected and recrystallized from ether to give 5-methyl-2-phenyloxazolo[4,5-b]pyridine, m.p. 148°–149° C.

EXAMPLE 64

2-(3-Acetamidophenyl)oxazolo[4,5-B]pyridine

A solution of 0.63 g. of 2-(3-aminophenyl)oxazolo[4,5-b]pyridine in 10 ml. of pyridine was treated with 0.35 ml. of acetic anhydride with stirring. After stirring over the weekend the mixture was diluted to 50 ml. with water. After stirring a short time and cooling, the precipitate was collected, washed with water and dried. Recrystallization from ethyl acetate gave 2-(3-acetamidophenyl)oxazolo[4,5-b]pyridine, m.p. 201.5°–202.5.

EXAMPLE 65

2-(2-Methylsulfinylphenyl)oxazolo[4,5-B]pyridine

A solution of 0.5 g. of 2-(2-methylthiophenyl)oxazolo[4,5-b]pyridine in 50 ml. of acetone was treated with 3 g. of sodium metaperiodate. After stirring over the weekend at room temperature, the mixture was diluted with 30 ml. of water. The acetone was distilled out and the resulting precipitate was recrystallized to give 2-(2-methylsulfinylphenyl)oxazolo[4,5-b]pyridine, m.p. 153.5°–155.5° C.

Employing the procedure as described in Example 65, but employing 2-(3-methylthiophenyl)oxazolo[4,5-b]pyridine as starting material, there is produced 2-(3-methylsulfinylphenyl)oxazolo[4,5-b]pyridine.

EXAMPLE 66

2-(2-Fluorophenyl)oxazolo[5,4-b]pyridine

Step A: Preparation of 3-(2-fluorobenzoylamino)-2-pyridone

To a solution of 3.3 g. (0.03 mole) of 3-amino-2-pyridone in 75 ml. of pyridine cooled in ice was added portionwise 6.3 g. (0.04 mole) of 2-fluorobenzoyl chloride over 5 minutes. After stirring for 15 hours at ambient temperature, the mixture was poured into ice-water. The resultant precipitate was collected by filtration, washed with water and recrystallized from ethanol to give 3-(2-fluorobenzoylamino)-2-pyridone, m.p. 223° C.

Step B: Preparation of 2-(2-fluorophenyl)oxazolo[5,4-b]pyridine

A solution of 5.4 g. of 3-(2-fluorobenzoylamino)-2-pyridone in 55 ml. of phosphorus oxychloride was refluxed for 5 hours. The excess phosphorus oxychloride was evaporated and the residue was treated with ice. The resulting precipitate was collected and recrystallized from benzenepetroleum ether to give 3.1 g. of 2-(2-fluorophenyl)oxazolo[5,4-b]pyridine, m.p. 118°–120° C.

Employing the procedure of Example 66, Steps A and B, but substituting for the 2-fluorobenzoyl chloride used in Step A, an equivalent amount of an acid chloride of formula R-COCl, there are produced the 3-(R-carbonylamino)-2-pyridones and 2-R-oxazolo[5,4-b]pyridines depicted in Table III in accordance with the following reactions:

Table III

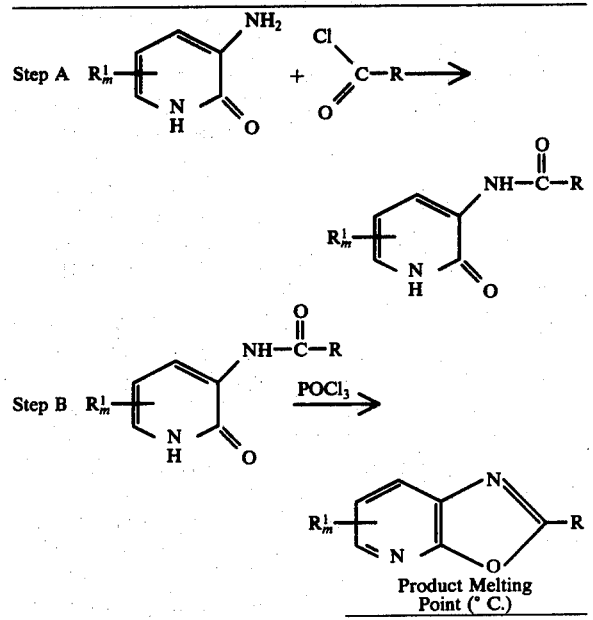

| Ex. | R¹ | R | Step A | Step B |
|---|---|---|---|---|
| 67 | H | 2-furyl | 252-253 | 125-127 |
| 68 | H | 2-nitrophenyl | 233-235 | 123-125 |
| 69 | H | 2-cyanophenyl | 282 | 146-147 |
| 70 | H | 4-nitrophenyl | 307(dec.) | 242-243 |
| 71 | H | 3-fluorophenyl | 214-215 | 90-91 |
| 72 | H | 4-methylthiophenyl | 228-229 | 157-159 |
| 73 | H | 4-methylphenyl | 210-211 | 115-116 |
| 74 | H | 4-cyanophenyl | 258-260 | 220-221 |
| 75 | H | 3-trifluoromethyl-phenyl | 205-207 | 147-149 |
| 76 | H | 3-methylphenyl | 199-200 | 101-102 |
| 77 | H | 4-fluorophenyl | 200-202 | 117-118 |
| 78 | H | 4-methoxyphenyl | 249-251 | 146-148 |
| 79 | H | 4-chlorophenyl | 215-217 | 153-154 |
| 80 | H | phenyl | 197-198 | 98-100 |
| 81 | H | 3,4-methylenedioxy-phenyl | 232-234 | 185.5-187 |
| 82 | H | 3-methoxyphenyl | 198-200 | 107-109 |
| 83 | H | 2-nitro-3-methylphenyl | | |
| 84 | H | 2-hydroxyphenyl | | |
| 85 | H | 3-hydroxyphenyl | | |
| 86 | H | 3-ethoxyphenyl | | |
| 87 | H | 3-methylaminophenyl | | |
| 88 | H | 3-di(methyl)aminophenyl | | |
| 89 | H | 2-methylthiophenyl | | |
| 90 | H | 3-methylthiophenyl | | |
| 91 | H | 2-mercaptophenyl | | |
| 92 | H | 3-mercaptophenyl | | |
| 93 | H | 4-mercaptophenyl | | |
| 94 | H | 2,3-dimethylphenyl | | |
| 95 | H | 3,5-dimethoxyphenyl | | |
| 96 | H | 2,3-dimethoxyphenyl | | |
| 97 | H | 2-methylphenyl | | |
| 98 | H | 2-chlorophenyl | 192-194 | 87-89 |
| 99 | H | 4-chloro-2-fluoro | | |
| 100 | H | 2,6-difluorophenyl | 247-248 | 113-115 |
| 101 | H | 2,4-dichlorophenyl | 253-254 | 135-137 |
| 102 | H | 3-chlorophenyl | 206-207 | 156-158 |
| 103 | H | 2-fluoro-3-methoxyphenyl | | |
| 104 | H | 2-fluoro-5-methoxyphenyl | | |
| 105 | H | 4-trifluoromethoxyphenyl | | |
| 106 | H | adamantan-1-yl | 246-247 | 70-71 |

EXAMPLE 107

5-Chloro-2-phenyloxazolo[5,4-b]pyridine

Step A: Preparation of 5-chloro-3-nitro-2-pyridone

2-Amino-5-chloropyridine (12.8 g., 0.1 mole) was added to 50 ml. of concentrated sulfuric acid. To this was slowly added with stirring 25 ml. of concentrated nitric acid. After the exothermic reaction subsided, the mixture was cooled and poured onto ice. The precipitate was collected and added to a mixture of 12 ml. of concentrated sulfuric acid and 150 ml. of water. To this solution cooled to 0° C., was added 7 g. of sodium nitrite portionwise and the resulting mixture was allowed to warm spontaneously to room temperature. After cooling the precipitate was collected and recrystallized from dimethyl formamideethanol to give 5-chloro-3-nitro-2-pyridone, m.p. 225-227°.

Step B: Preparation of 3-benzoylamino-5-chloro-2-pyridone

5-Chloro-3-nitro-2-pyridone (5.3 g.) was hydrogenated in 225 ml. of ethanol and 6 ml. of acetic acid in the presence of 0.6 g. of 5% palladium-on-carbon. The catalyst was removed by filtration and the filtrate was concentrated to dryness. The residue was dissolved in 75 ml. of pyridine, cooled in ice and treated over 15 minutes with 4.8 g. of benzoyl chloride. The ice bath and reaction mixture were allowed to warm to room temperature spontaneously. The mixture was poured onto 200 g. of ice. On dilution with 500 ml. of water an oil separated which on washing with water solidified (4 g.). The crude 3-benzoylamino-5-chloro-2-pyridone was used directly in the next step.

Step C: Preparation of 5-chloro-2-phenyloxazolo[5,4-b]pyridine

A mixture of 2.1 g. of the crude 3-benzoylamino-5-chloro-2-pyridone and 7 g. of poly phosphoric acid was heated 10 minutes at 140°-150° C. Ice-water was added, the precipitate was collected on a filter, and the solids were extracted with hot benzene. The benzene was evaporated and the residue was taken up in ether, filtered through Al₂O₃ and concentrated to dryness to give 300 mg. of 5-chloro-2-phenyloxazolo[5,4-b]pyridine, m.p. 150°-151° C.

EXAMPLE 108

4-Methyl-2-phenyloxazolo[5,4-b]pyridine

Step A: Preparation of 3-benzoylamino-4-methyl-2-pyridone

4-Methyl-3-nitro-2-pyridone (7.7 g.) was hydrogenated in 50 ml. of methanol with 0.25 g. of 5% palladium-on-carbon. The catalyst was removed by filtration and the solvent was evaporated.

The solid residue was dissolved in 60 ml. of pyridine, cooled to 20° C. and treated with 6.5 ml. of benzoyl chloride. After standing overnight the mixture was poured into 200 ml. of water and ice. The precipitate (5 g.) was collected and recrystallized from methanol to give 3-benzoylamino-4-methyl-2-pyridone, m.p. 264°-265° C.

Step B: Preparation of 4-methyl-2-phenyloxazolo[5,4-b]pyridine

A solution of 3 g. of 3-benzoylamino-4-methyl-2-pyridone in 30 ml. of phosphorus oxychloride was heated on the steam bath for 66 hours. The mixture was poured onto ice, and neutralized with ammonium hydroxide. The precipitate was collected and recrystallized from methanol to give 1.4 g. of 4-methyl-2-phenyloxazolo[5,4-b]pyridine, m.p. 91°-92° C.

EXAMPLE 109

5-Nitro-2-phenyloxazolo[5,4-b]pyridine

Step A: Preparation of 3-amino-5-nitro-2-pyridone

A solution of 5.5 g. of 3,5-dinitro-2-pyridone in 200 ml. of methanol was adjusted to pH 8 with ammonium hydroxide. At 60°-65° C., there was added slowly a solution of 10.8 g. of sodium sulfide nonahydrate in 30 ml. of water. After 1 hour at 60°-65° C. the solvent was evaporated and the residue was extracted with hot benzene and acetic acid to neutralize any sodium salt. The benzene was decanted and cooled to give a precipitate. Recrystallization from methanol gave 3-amino-5-nitro-2-pyridone, m.p. 200°-201° C.

Step B: Preparation of 3-benzoylamino-5-nitro-2-pyridone

A solution of 100 mg. of 3-amino-5-nitro-2-pyridone in 1.5 ml. of pyridine was cooled and treated with 200 mg. of benzoyl chloride. After 2 hours water was added. The oil that separated was washed with water and triturated with ether. The resultant solid was recrystallized from ethyl acetate to give 3-benzoylamino-5-nitro-2-pyridone, m.p. 267°-268° C.

Step C: Preparation of 5-Nitro-2-phenyloxazolo[5,4-b]pyridine

A mixture of 300 mg. of 3-benzoylamino-5-nitro-2-pyridone and 1.5 g. of polyphosphoric acid was heated at 180° C. for 15 minutes. The mixture was cooled, treated with ice and the precipitate was collected. The precipitate was dissolved in ether, filtered through Al$_2$O$_3$ and evaporated to give 5-nitro-2-phenyloxazolo[5,4-b]pyridine, m.p. 219°-220° C.

EXAMPLE 110

6-Methyl-2-phenyloxazolo[5,4-b]pyridine

Step A: Preparation of 6-methyl-3-nitro-2-pyridone

A solution of 24 g. of 2-amino-6-methyl-3-nitro-pyridine in 25 ml. of concentrated sulfuric acid and 380 ml. of water was cooled to 0° C. and treated with 11 g. of sodium nitrite in 25 ml. of water. The temperature spontaneously rose to 45° C. After cooling, the precipitate of 6-methyl-3-nitro-2-pyridone was collected (m.p. 222°-223° C.) and used directly in the next stop.

Step B: Preparation of 3-benzoylamino-6-methyl-2-pyridone

6-Methyl-3-nitro-2-pyridone (7.7 g.) was hydrogenated in 50 ml. of methanol in the presence of 0.25 g. of 5% palladium on carbon. The catalyst was removed by filtration and the filtrate was evaporated to dryness.

The residue was taken up in 60 ml. of pyridine, cooled to 20° C. and treated with 6.5 ml. of benzoyl chloride. After 2 hours at 20° C., the mixture was poured onto ice. The precipitate was collected and dried to give 9 g. of 3-benzoylamino-6-methyl-2-pyridone, m.p. 241°-242° C.

Step C: Preparation of 6-methyl-2-phenyloxazolo[5,4-b]pyridine

A solution of 5 g. of 3-benzoylamino-6-methyl-2-pyridone in 50 ml. of phosphorus oxychloride was warmed on the steam bath for 20 hours. The solution was poured slowly onto ice with good stirring. The precipitate was collected on a filter and recrystallized from aqueous ethanol to give 6-methyl-2-phenyloxazolo[5,4-b]pyridine, m.p. 71°-73° C.

EXAMPLE 111

5-Trifluoromethyl-2-phenyloxazolo[5,4-b]pyridine

Step A: Preparation of 6-chloronicotinic acid

To a stirred suspension of 28 g. of 6-hydroxynicotinic acid in 193 ml. of phosphorus oxychloride was added 83 g. of phosphorus pentachloride portionwise. After stirring 1 hour at room temperature the mixture was heated on a steam-bath overnight. Excess phosphorus oxychloride was removed in vacuo and the warm residue was added to about 1.2 l. of crushed ice and the mixture was allowed to warm to room temperature by stirring overnight. The precipitate was collected by filtration, washed with water and dried to give 29 g. (92%) of 6-chloronicotinic acid, m.p. 187.5°-189 (dec.).

Step B: Preparation of 2-chloro-5-chloro-5-trifluoromethylpyridine

A mixture of 29 g. of 6-chloronicotinic acid, 130 g. of sulfur tetrafluoride and 18 ml. of hydrofluoric acid was heated in a bomb at 150° C. for 16 hours. After cooling and venting the reaction mixture was treated with cooling to about 40° C. with 2.5 N sodium hydroxide solution to pH 9. The mixture was extracted with chloroform, and the extract was filtered, dried and concentrated to a yellow oil (17 g.) which was used directly in the next step.

Step C: Preparation of 5-trifluoromethyl-2-pyridone

A solution of 5.5 g. of 2-chloro-5-trifluoromethyl pyridine in 100 ml. of acetic acid was treated under nitrogen with 5.5 g. of silver acetate. The mixture was heated at 140° C. for about 45 hours. The hot mixture was filtered and the filter cake was washed with acetic acid. The combined filtrate and washings were concentrated to dryness. The residue was distributed between chloroform and water and the mixture was basified with solid sodium bicarbonate. The mixture was filtered, the layers were separated and the aqueous phase was reextracted with chloroform. The combined chloroform layers were dried and concentrated to dryness. The residue was recrystallized from acetone to give 2.5 g. of 5-trifluoromethyl-2-pyridone, m.p. 145°-147.8° C.

Step D: Preparation of 3-nitro-5-trifluoromethyl-2-pyridone

To 0.95 l. of stirred fuming nitric acid was added 29 g. of 5-trifluoromethyl-2-pyridone over 1 hour, and stirring was continued for 75 hours. The fuming nitric acid was evaporated and the residue was triturated with acetone. The acetone was evaporated to about 60 ml. and the precipitate was collected on a filter and washed with a 5:1 mixture of methylene chloride:acetone and dried and used directly in the next step.

Step E: Preparation of 3-benzoylamino-5-trifluoromethyl-2-pyridone

3-Nitro-5-trifluoromethyl-2-pyridone (3.12 g.) was reduced in 50 ml. ethanol in the presence of Raney nickel. The catalyst was removed by filtration, and the filtrate was concentrated to dryness.

The residue was taken up in 10 ml. of pyridine, cooled to 5° C. and slowly treated with 2.0 ml. of benzoyl chloride. After standing overnight the mixture was treated with ice and water to give an oil. The aqueous phase was decanted, and the oil was triturated with ether. The solid was collected and recrystallized from methanol to give 3-benzoylamino-5-trifluoromethyl-2-pyridone, m.p. 207°-210° C.

Step F: Preparation of 5-trifluoromethyl-2-phenyloxazolo [5,4-b]pyridine

A solution of 300 mg. of 3-benzoylamino-5-trifluoromethyl-2-pyridone in 4.5 ml. of phosphorus oxychloride was refluxed for 16 hours. The excess phosphorus oxychloride was evaporated and the residue was treated with ether and dilute sodium hydroxide solution. The ether phase was separated, dried and evaporated. The residue was recrystallized from ethyl acetate to give 5-trifluoromethyl-2-phenyloxazolo [5,4-b]pyridine, m.p. 127°-129° C.

EXAMPLE 112

5Amino-2-phenyloxazolo [5,4-b]pyridine

A solution of 361 mg. of 5-nitro-2-phenyloxazolo [5,4-b]pyridine in 30 ml. of methanol was hydrogenated over 0.2 g. of 5% palladium-on-carbon catalyst. The catalyst was removed by filtration, and the filtrate was concentrated to dryness. The residue was recrystallized from methanol to give 5-amino-2-phenyloxazolo [5,4-b]pyridine, m.p. 210° C.

EXAMPLE 113

5-Benzoylamino-2-phenyloxazolo [5,4-b]pyridine

A solution of 80 mg. of 5-amino-2-phenyloxazolo [5,4-b]pyridine in 1 ml. of pyridine was treated with 0.07 ml. of benzoyl chloride. After standing 1 hour the mixture was diluted with ice-water. The precipitate was collected and recrystallized from methanol to give 5-benzoylamino-2-phenyloxazolo [5,4-b]pyridine, m.p. 191°-192° C.

EXAMPLE 114

2,5-Diphenyloxazolo [5,4-b]pyridine

A mixture of 180 mg. of 5-amino-2-phenyloxazolo [5,4-b]pyridine, 10 ml. of benzene and 0.2 ml. of isoamyl nitrate was refluxed for 1½ hours. The hot solution was filtered and concentrated to dryness. The residue was extracted with ether and the extract was filtered through aluminum oxide and concentrated to dryness. The crystalline residue was recrystallized from ethyl acetate to give 2,5-diphenyloxazolo [5,4-b]pyridine, m.p. 151°-152° C.

EXAMPLE 115

5-Isopropoxycarbonylamino-2-phenyloxazolo [5,4-b]pyridine

A mixture of 300 mg. of 5-amino-2-phenyloxazolo [5,4-b]pyridine and 3 ml. of pyridine was cooled in ice and to it was added 0.2 ml. of isopropylchloroformate. The mixture was allowed to age in the refrigerator for 5 days, and diluted with ice and water. The precipitate was collected and recrystallized from isopropanol to give 5-isopropoxycarbonylamino-2-phenyloxazolo [5,4-b]pyridine, m.p. 210°-211° C.

EXAMPLE 116

2-(4-Carbamylphenyl)oxazolo [5,4-b]pyridine

A solution of 600 mg. of 2-(4-cyanophenyl)oxazolo [5,4-b]pyridine in 8 ml. of concentrated sulfuric acid was allowed to stand at room temperature for 16 hours. The solution was poured onto ice and the white precipitate was collected on a filter to give 2-(4-carbamylphenyl)oxazolo [5,4-b]pyridine, m.p. 315° C. (dec.).

EXAMPLE 117

2-(4-Dimethylaminophenyl)oxazolo [5,4-b]pyridine

A mixture of 2.4 grams of 2-(4-nitrophenyl)oxazolo [5,4-b]pyridine, 7 ml. of 37% formaldehyde solution, 5 ml. of acetic acid and 0.25 grams of Raney nickel and 125 ml. of methanol was hydrogenated. The catalyst was removed by filtration and the filtrate was concentrated to dryness. The residue was extracted with water and the water insoluble residue as recrystallized form chloroform-petroleum ether to give 2-(4-dimethylaminophenyl)oxazolo [5,4-b]pyridine, m.p. 168°-170° C.

EXAMPLE 118

2-(2-Aminophenyl)oxazolo [5,4-b]pyridine

A mixture of 700 mg. of 2-(2-nitrophenyl)oxazolo [5,4-b]pyridine in 50 ml. of ethanol was hydrogenated over 150 mg. of 5% palladium on carbon catalyst. The catalyst was removed by filtration and the solvent was concentrated to dryness. The residue was recrystallized from chloroform-petroleum ether to give 2-(2-aminophenyl)oxazolo [5,4-b]pyridine, m.p. 142°-144° C.

EXAMPLE 119

2-(2-Benzoylaminophenyl)oxazolo [5,4-b]pyridine

An ice cold solution of 1 gram of 2-(2-aminophenyl)oxazolo [5,4-b]pyridine in 15 ml. of dry pyridine was treated with 1 gram of benzoyl chloride slowly. The reaction mixture was diluted with ice-water and stirred for 10 minutes and the resulting solid was collected on a filter and recrystallized from benzene to give 2-(2-benzoylaminophenyl)oxazolo [5,4-b]pyridine, m.p. 197°-198° C.

EXAMPLE 120

5-Chloro-2-(2-fluorophenyl)oxazolo [5,4-b]pyridine

Step A: Preparation of 5-chloro-3-(2-fluorobenzoylamino)-2-pyridone

A solution of 1.7 grams of 5-chloro-3-nitro-2-pyridone in 75 ml. of ethanol and 2 ml. of acetic acid was hydrogenated over 0.2 grams of 5% palladium on carbon catalyst. The catalyst was removed by filtration and the solvent was evaporated to dryness.

The dried residue was dissolved in 30 ml. of pyridine, cooled in ice and treated with 1.6 grams of 2-fluorobenzoyl chloride over 5 minutes. The mixture was stirred at ambient temperature for about 16 hours and poured into ice-water. The resulting precipitate was collected on a filter (1.5 g.) and used directly in the next step without purification.

Step B: Preparation of 5-chloro-2-(2-fluorophenyl)oxazolo [5,4-b]pyridine

A mixture of 1.5 grams of the above amide and 5 ml. of polyphosphoric acid was heated at 160° C. for 10 minutes. After cooling, the mixture was added to ice water. The precipitate was collected and extracted with 75 ml. of hot benzene and the extract was decolorized with activated carbon and evaporated to dryness. The residue was dissolved in methylene chloride and filtered through aluminum oxide and the filter was washed with ether. The product, 5-chloro-2-(2-fluorophenyl)-oxazolo [5,4-b]pyridine crystallized from the filtrate and had melting point 140°-141° C.

EXAMPLE 121

5-Dimethylamino-2-phenyloxazolo [5,4-b]pyridine

5-Nitro-2-phenyloxazolo [5,4-b]pyridine (1.2 g.) in 75 ml. of methanol. 75 ml. of benzene, 5 ml. of acetic acid and 8 ml. of 37% formaldehyde solution was hydrogenated over 1.5 teaspoonsful of Raney nickel. The catalyst was removed by filtration and the filtrate was diluted with 10 ml. of water and basified with solid sodium bicarbonate. The mixture was concentrated to dryness. The residue was crystallized from ethyl acetate to give 5-dimethylamino-2-phenyloxazolo [5,4-b]pyridine, m.p. 127°-129° C.

EXAMPLE 122

5-Methoxy-6-methyl-2-phenyloxazolo [5,4-b]pyridine

Step A: Preparation of 3-methoxy-2-methyl-6-nitropyridine

To an ice-cold mixture of 3 ml. of concentrated sulfuric acid and 3 ml. of fuming nitric acid, was added 0.5 g. of 3-methoxy-2-methylpyridine over 5 minutes. After warming spontaneously to room temperature the mixture was heated at 55°–60° C. for 6 hours. The mixture was cooled and added to 35 ml. of ice-water. After stirring 2 hours, the precipitate was collected and dried to give 3-methoxy-2-methyl-6-nitropyridine, m.p. 99°–100.5° C.

Step B: Preparation of 6-amino-3-methoxy-2-methylpyridine

3-Methoxy-2-methyl-6-nitropyridine (0.317 g.) in 20 ml. of methanol, was hydrogenated over 0.1 g. of 5% palladium-on-carbon catalyst. The catalyst was removed by filtration and the filtrate was concentrated to dryness to give 6-amino-3-methoxy-2-methylpyridine, which was used directly in the next step.

Step C: Preparation of 5-methoxy-6-methyl-2-pyridone

To an ice-cold mixture of 0.2 ml. of concentrated sulfuric acid, 2.0 ml. of water and 138 mg. of 6-amino-3-methoxy-2-methylpyridine was added a solution of 75 mg. of sodium nitrate in 1 ml. of water. The cold solution was allowed to warm to room temperature overnight. The mixture was diluted with a little water and made basic with solid sodium bicarbonate. The mixture was extracted with methylene chloride, and the extract was concentrated to dryness to give 120 mg. of 5-methoxy-6-methyl-2-pyridone, which was used directly in the next step.

Step D: Preparation of 5-methoxy-6-methyl-3-nitro-2-pyridone

To a mixture of 4.2 g. of 5-methoxy-6-methyl-2-pyridone in 50 ml. of ice cold concentrated sulfuric acid was added 2.5 ml. of concentrated nitric acid dropwise at about 50° C. over 60 minutes. Stirring in the cold was continued overnight. The mixture was added to about 700 g. of ice with stirring. After about 30 minutes the precipitate was collected, washed with water and dried to give 3.7 g. of 5-methoxy-6-methyl-3-nitro-2-pyridione, which was used directly in the next step.

Step E: Preparation of 3-benzoylamino-5-methoxy-6-methyl-2-pyridone

5-Methoxy-6-methyl-3-nitro-2-pyridone (1.84 g.) in 100 ml. of methanol was hydrogenated over 0.5 g. of 5% palladium-on-carbon catalyst. The catalyst was removed by filtration and the filtrate was concentrated to dryness. The residue was dissolved in 15 ml. of pyridine and treated in the cold with 1.2 ml. of benzoyl chloride. After standing overnight at ice temperature the mixture was diluted with water. The resulting precipitate was collected and recrystallized from ethanol. This material was extracted several times with ether, and the isoluble material was recrystallized from ethanol to give 3-benzoylamino-5-methoxy-6-methyl-2-pyridone, m.p. 247°–248° C.

Step F: Preparation of 5-methoxy-6-methyl-2-phenyloxazolo [5,4-b]pyridine

A mixture of 200 mg. of 3-benzoylamino-5-methoxy-6-methyl-2-pyridone and 3 ml. of phosphorus oxychloride was heated on the steam bath for 20 hours. The mixture was concentrated to dryness and the residue was taken up in ether, basified with ammonium hydroxide and diluted with water. The ether was separated, and the aqueous phase was extracted 3 times with ether. The combined ether phases were dried and concentrated to dryness to give 5-methoxy-6-methyl-2-phenyloxazolo [5,4-b]pyridine, m.p. 167°–168° C.

EXAMPLE 123

2-(2-Fluorophenyl)-5-methyloxazolo [5,4-b]pyridine

Step A: Preparation of 3-(2-fluorobenzoylamino)-5-methyl-2-pyridone

A solution of 3.1 g. of 3-amino-5-methyl-2-pyridone in 25 ml. of pyridine was cooled in ice and treated with 4.5 g. of 2-fluorobenzoyl chloride dropwise. After stirring about 3 hours at room temperature, the mixture was diluted with 200 ml. of ice-water. After 0.5 hour the precipitate was collected, washed with water, dried and recrystallized from ethanol to give 3-(2-fluorobenzoylamino)-5-methyl-2-pyridone, m.p. 230°–232° C.

Step B: Preparation of 2-(2-flurorphenyl)-5-methyloxazolo [5,4-b]pyridine

A mixture of 1.8 g. of 3-(2-fluorobenzoylamino)-5-methyl-2-pyridone and 25 ml. of phosphorus oxychloride was refluxed of 1.5 hours. The excess phosphorus oxychloride was evaporated and the residual oil was triturated with cold water. The precipitate was collected and recrystallized from benzene-petroleum ether to give 2-(2-fluorophenyl)-5-methyloxazolo [5,4-b]pyridine, m.p. 136°–137° C.

EXAMPLE 124

2-Phenyloxazolo [4,5-c]pyridine

Step A: Preparation of 34-pyridone

A solution of 50 grams of 4-hydroxypyridine in 500 ml. of water and 90 ml. of concentrated nitric acid was concentrated in an evaporating dish on a steam bath to about 350 ml. The mixture was cooled and the precipitate was collected on a filter to give 55 grams of 4-hydroxypyridine nitrate.

To a cold solution of 35 ml. of fuming sulfuric acid and 45 ml. of fuming nitric acid was added 35 grams of the 4-hydroxypyridine nitrate. After allowing the mixture to warm to room temperature over night it was heated on a steam bath for 2¼ hours. It was cooled and poured onto 500 grams of ice. The resulting precipitate was collected on a filter, washed with a minimum of water and recrystallized from water to give 3-nitro-4-pyridone, m.p. 282°–284° C.

Step B: Preparation of 3-amino-4-pyridone

3-Nitro-4-pyridone (7.0 g.) in 100 ml. of methanol was hydrogenated over 0.5 grams of 5% palladium-on-carbon catalyst. The catalyst was removed by filtration and the filtrate was concentrated to dryness to give crude 3-amino-4-pyridone.

Step C: Preparation of 2-phenyloxazolo [4,5-c]pyridine

A mixture of 6 grams of 3-amino-4-pyridone and 40 grams of benzoic anhydride was heated to 245° C. for 20 minutes. After cooling to about 100° C. the mixture was poured into 200 ml. of benzene and the mixture was extracted 6 times with 2.5 N hydrochloric acid. The combined acid extracts were filtered and the filtrate was made basic with ammonium hydroxide. The resulting precipitate was collected and recrystallized from ethyl acetate to give 2-phenyloxazolo [4,5-c]pyridine, m.p. 118°–121° C.

EXAMPLE 125

2-(2-Fluorophenyl)oxazolo [4,5-c]pyridine

Step A: Preparation of 3-(2-fluorobenzoylamino)-4-pyridone

A solution of 5.3 grams of 3-nitro-4-pyridone in 100 mls. of ethanol was hydrogenated over 0.5 grams of 5% palladium-on-carbon catalyst. The catalyst was removed by filtration and the filtrate was evaporated to dryness. The oily residue was taken up in 75 ml. of dry pyridine, cooled in ice and stirred as 6.3 grams of 2-fluorobenzoylchloride was added over 10 minutes. Stirring was continued at ice-bath temperature for another 20 minutes and then at room temperature for about 16 hours. The mixture was poured into ice water and the resulting precipitate was collected on a filter and recrystallized from dimethylformamide-ether mixture to give 3-(2-fluorobenzoylamino)-4-pyridone, m.p. 298° C.

Step B: Preparation of 2-(2-fluorophenyl)oxazolo [4,5-c]pyridine

A mixture of 1 gram of 3-(24-pyridone and 4 grams of polyphosphoric acid was heated at 160° C. for 10 minutes. The mixture was added to ice water to decompose excess polyphosphoric acid, filtered and neutralized with solid sodium bicarbonate. The resulting precipitate was collected on a filter and recrystallized from benzene-petroleum ether to give 2-(2-fluorophenyl)oxazolo [4,5-c]pyridine, m.p. 110°-111° C.

Employing substantially the procedure of Example 125, Steps A and B, but substituting for the 2-flurorbenzoyl chloride used in Step A an equivalent amount of an acid chloride of formula R-COCL, there are produced the 3-(R-carbonylamino)-4-hydroxypyridines and 2-R-oxazolo [4,5-c]pyridines depicted in Table IV in accordance with the following reactions:

Table IV

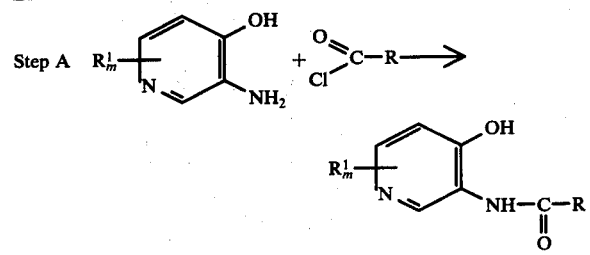

| Example | R¹ | R |
|---|---|---|
| 126 | H | 2-furyl |
| 127 | H | 2-nitrophenyl |
| 128 | H | 2-cyanophenyl |
| 129 | H | 4-nitrophenyl |
| 130 | H | 3-fluorophenyl |
| 131 | H | 4-methylthiophenyl |
| 132 | H | 4-methylphenyl |
| 133 | H | 4-cyanophenyl |
| 134 | H | 3-triflouromethylphenyl |
| 135 | H | 3-methylphenyl |
| 136 | H | 4-fluorophenyl |
| 137 | H | 4-methoxyphenyl |
| 138 | H | 4-chlorophenyl |

Table IV-continued

| Example | R¹ | R |
|---|---|---|
| 139 | H | phenyl |
| 140 | H | 3,4-methylenedioxyphenyl |
| 141 | H | 3-methoxyphenyl |
| 142 | H | 2-nitro-3-methylphenyl |
| 143 | H | 2-hydroxyphenyl |
| 144 | H | 3-hydroxyphenyl |
| 145 | H | 3-ethoxyphenyl |
| 146 | H | 3-methylaminophenyl |
| 147 | H | 3-di(methyl)aminophenyl |
| 148 | H | 2-methylthiophenyl |
| 149 | H | 3-methylthiophenyl |
| 150 | H | 2-mercaptophenyl |
| 151 | H | 3-mercaptophenyl |
| 152 | H | 4-mercaptophenyl |
| 153 | H | 2,3-dimethylphenyl |
| 154 | H | 3,5-dimethoxyphenyl |
| 155 | H | 2,3-dimethoxyphenyl |
| 156 | H | 2-methylphenyl |
| 157 | H | 2-chlorophenyl |
| 158 | H | 4-chloro-2-fluoro |
| 159 | H | 2,6-difluorophenyl |
| 160 | H | 2,4-dichlorophenyl |
| 161 | H | 3-chlorophenyl |
| 162 | H | 2-fluoro-3-methoxyphenyl |
| 163 | H | 2-fluoro-5-methoxyphenyl |
| 164 | H | 4-trifluoromethoxyphenyl |
| 165 | H | adamantan-1-yl |

EXAMPLE 166

2-(2-Fluorophenyl)thiazole [5,4-b]pyridine 3-(2-Fluorobenzoylamino)-2-pyridone (2 g.), 60 ml. of xylene and 15 ml of pyridine were heated until solution was complete. To this solution was added 6.5 grams of phosphorus pentasulfide and the mixture was heated at reflux for 16 hours. The reaction mixture was decanted from a gummy residue while hot, and the solvents were concentrated to dryness. The crystalline residue was recrystallized from ethanol to give 2-(2-fluorophenyl)-thiazolo [5,4-b]pyridine, m.p. 119°-121° C.

Employing the procedure of Example 166 but substituting for the 3-(2-flurorobenzoylamino)-2-pyridone used therein, an equivalent amount of the 3-(R-carbonylamino)-2-pyridones described in Examples 67–106 respectively, there are produced the 2-R-thiazolo [5,4-b]pyridines depicted in Table V in accordance with the following equation:

Table V

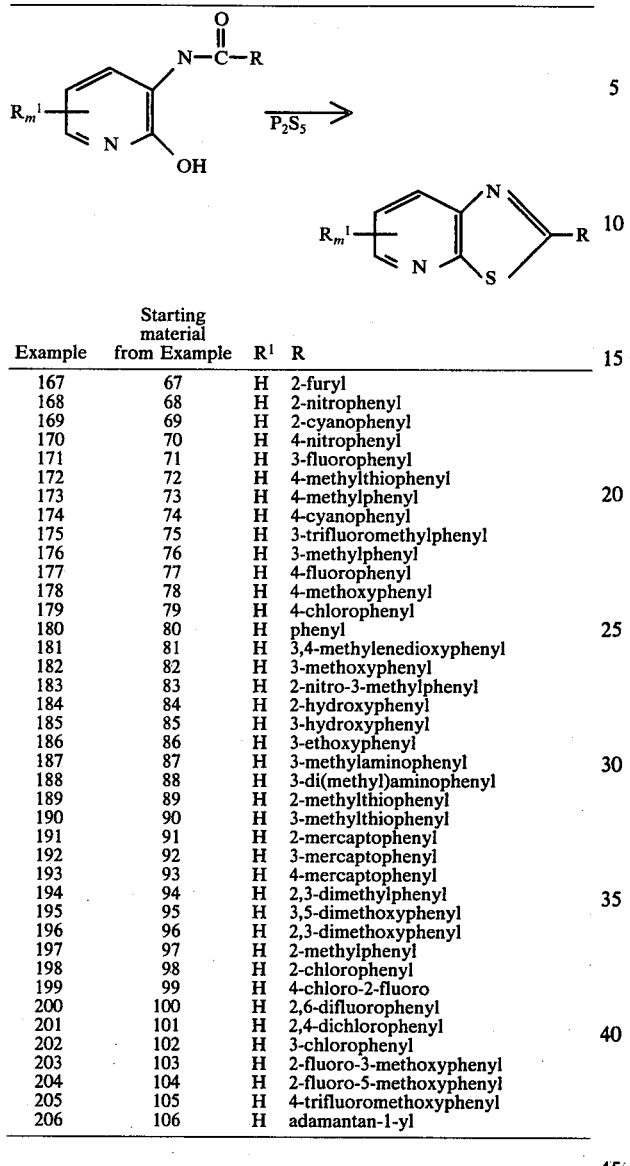

| Example | Starting material from Example | R¹ | R |
|---|---|---|---|
| 167 | 67 | H | 2-furyl |
| 168 | 68 | H | 2-nitrophenyl |
| 169 | 69 | H | 2-cyanophenyl |
| 170 | 70 | H | 4-nitrophenyl |
| 171 | 71 | H | 3-fluorophenyl |
| 172 | 72 | H | 4-methylthiophenyl |
| 173 | 73 | H | 4-methylphenyl |
| 174 | 74 | H | 4-cyanophenyl |
| 175 | 75 | H | 3-trifluoromethylphenyl |
| 176 | 76 | H | 3-methylphenyl |
| 177 | 77 | H | 4-fluorophenyl |
| 178 | 78 | H | 4-methoxyphenyl |
| 179 | 79 | H | 4-chlorophenyl |
| 180 | 80 | H | phenyl |
| 181 | 81 | H | 3,4-methylenedioxyphenyl |
| 182 | 82 | H | 3-methoxyphenyl |
| 183 | 83 | H | 2-nitro-3-methylphenyl |
| 184 | 84 | H | 2-hydroxyphenyl |
| 185 | 85 | H | 3-hydroxyphenyl |
| 186 | 86 | H | 3-ethoxyphenyl |
| 187 | 87 | H | 3-methylaminophenyl |
| 188 | 88 | H | 3-di(methyl)aminophenyl |
| 189 | 89 | H | 2-methylthiophenyl |
| 190 | 90 | H | 3-methylthiophenyl |
| 191 | 91 | H | 2-mercaptophenyl |
| 192 | 92 | H | 3-mercaptophenyl |
| 193 | 93 | H | 4-mercaptophenyl |
| 194 | 94 | H | 2,3-dimethylphenyl |
| 195 | 95 | H | 3,5-dimethoxyphenyl |
| 196 | 96 | H | 2,3-dimethoxyphenyl |
| 197 | 97 | H | 2-methylphenyl |
| 198 | 98 | H | 2-chlorophenyl |
| 199 | 99 | H | 4-chloro-2-fluoro |
| 200 | 100 | H | 2,6-difluorophenyl |
| 201 | 101 | H | 2,4-dichlorophenyl |
| 202 | 102 | H | 3-chlorophenyl |
| 203 | 103 | H | 2-fluoro-3-methoxyphenyl |
| 204 | 104 | H | 2-fluoro-5-methoxyphenyl |
| 205 | 105 | H | 4-trifluoromethoxyphenyl |
| 206 | 106 | H | adamantan-1-yl |

EXAMPLE 207

2-(2-Fluorophenyl)thiazolo [4,5-c]pyridine

3-Nitro-4-pyridine (2.8 grams) in 50 ml. of methanol was hydrogenated over 0.2 grams of palladium-on-carbon catalyst (5%). The catalyst was removed by filtration and the filtrate was concentrated to dryness.

The residue was taken up in 25 ml. of pyridine by heating to about 80° C. After cooling to 10°-15° C. 3 ml. of 2-fluorobenzoylchloride was added slowly while maintaining the temperature below 20° C. After standing overnight, ice was added and the resulting mixture was filtered and the filter cake was washed with water and recrystallized from methanol to give 3-(2-fluorobenzoylamino)-4-pyridone, m.p. 297°-299° C.

The above amide was dissolved in 100 ml. of xylene and 30 ml. of pyridine and heated to 130° C. and treated slowly with 10.5 grams of phosphorus pentasulfide. After heating under reflux for 18 hours the hot solution was decanted and the solvents were concentrated to dryness. The crystalline residue was extracted with ether. The ether extracts were combined, concentrated to dryness and the resiude was crystallized from ethanol to give, 2-(2-fluorophenyl)thiazolo [4,5-c]pyridine, m.p. 116°-117° C.

Employing the procedure of Example 207, but substituting for the 3-(2-fluorobenzoylamino)-4-pyridone used therein the 3-(R-carbonylamino)-4-pyridones described in Examples 126-165 respectively, there are produced the 2-R-thiazolo [4,5-c]pyridines depicted in Table VI in accordance with the following equation:

Table VI

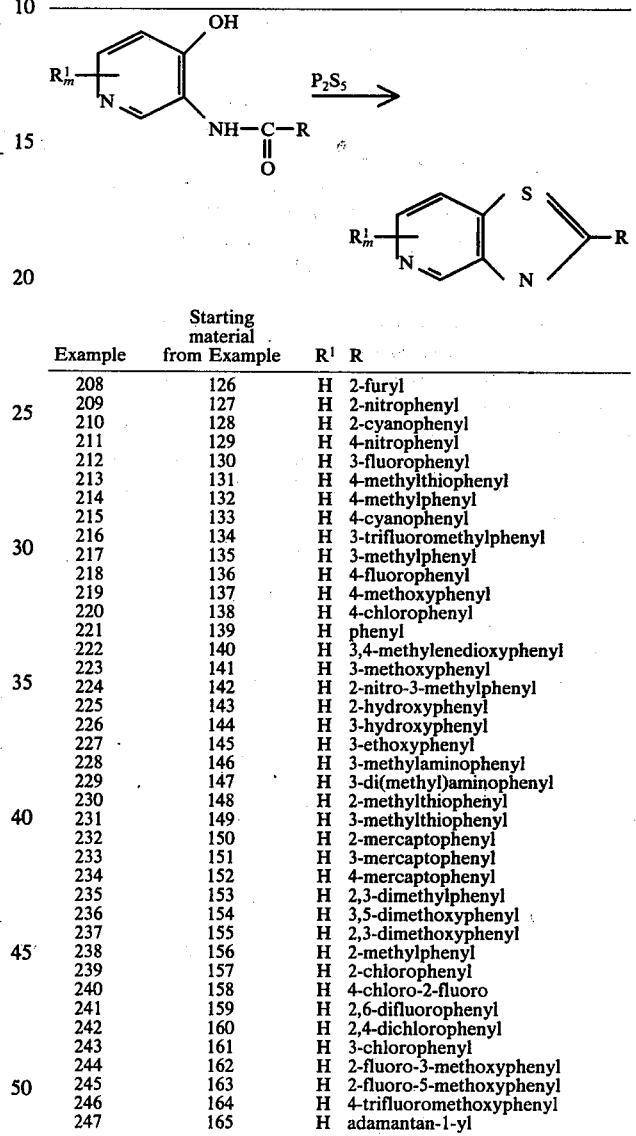

| Example | Starting material from Example | R¹ | R |
|---|---|---|---|
| 208 | 126 | H | 2-furyl |
| 209 | 127 | H | 2-nitrophenyl |
| 210 | 128 | H | 2-cyanophenyl |
| 211 | 129 | H | 4-nitrophenyl |
| 212 | 130 | H | 3-fluorophenyl |
| 213 | 131 | H | 4-methylthiophenyl |
| 214 | 132 | H | 4-methylphenyl |
| 215 | 133 | H | 4-cyanophenyl |
| 216 | 134 | H | 3-trifluoromethylphenyl |
| 217 | 135 | H | 3-methylphenyl |
| 218 | 136 | H | 4-fluorophenyl |
| 219 | 137 | H | 4-methoxyphenyl |
| 220 | 138 | H | 4-chlorophenyl |
| 221 | 139 | H | phenyl |
| 222 | 140 | H | 3,4-methylenedioxyphenyl |
| 223 | 141 | H | 3-methoxyphenyl |
| 224 | 142 | H | 2-nitro-3-methylphenyl |
| 225 | 143 | H | 2-hydroxyphenyl |
| 226 | 144 | H | 3-hydroxyphenyl |
| 227 | 145 | H | 3-ethoxyphenyl |
| 228 | 146 | H | 3-methylaminophenyl |
| 229 | 147 | H | 3-di(methyl)aminophenyl |
| 230 | 148 | H | 2-methylthiophenyl |
| 231 | 149 | H | 3-methylthiophenyl |
| 232 | 150 | H | 2-mercaptophenyl |
| 233 | 151 | H | 3-mercaptophenyl |
| 234 | 152 | H | 4-mercaptophenyl |
| 235 | 153 | H | 2,3-dimethylphenyl |
| 236 | 154 | H | 3,5-dimethoxyphenyl |
| 237 | 155 | H | 2,3-dimethoxyphenyl |
| 238 | 156 | H | 2-methylphenyl |
| 239 | 157 | H | 2-chlorophenyl |
| 240 | 158 | H | 4-chloro-2-fluoro |
| 241 | 159 | H | 2,6-difluorophenyl |
| 242 | 160 | H | 2,4-dichlorophenyl |
| 243 | 161 | H | 3-chlorophenyl |
| 244 | 162 | H | 2-fluoro-3-methoxyphenyl |
| 245 | 163 | H | 2-fluoro-5-methoxyphenyl |
| 246 | 164 | H | 4-trifluoromethoxyphenyl |
| 247 | 165 | H | adamantan-1-yl |

EXAMPLE 248

2-(2-Cyanopyrid-3-yl)Oxazolo[5,4-b]Pyridine

Step A: Preparation of 3-(2-chloronicotinoylamino)-2-Pyridone

The acid chloride of 2-chloronicotinic acid was prepared by refluxing 11 g. (0.07 mole) of 2-chloronicotinic acid in 80 ml. of thionyl chloride for 1.5 hours. After evaporating to dryness, the oily residue was dissolved in 50 ml. of ether. The ether solution was added to a stirred ice-cold solution of 7.7 g. (0.07 mole) of 3-amino-2- pyridone in 80 ml. of dry pyridine during 15 minutes. After 30 more minutes at ice temperature and 4 hours at room temperature, it was allowed to stand overnight in an open dish. The crystalline residue was extracted with water and the solid residue (12.9 g.) was collected and recrystallized from dimethyl formamide-ether to give gray crystals of 3-(2-chloronicotinoylamino)-2-pyridone, m.p. 295° C.

Step B: Preparation of 2-(2-chloropyrid-3-yl)oxazolo[5,4-b]pyridine

The amide from Step A (5.0 g.) in 50 ml. of phosphorus oxychloride was refluxed for 2 hours. After concentration in vacuo, the residue was treated with ice and solid sodium bicarbonate and a gray precipitate (3.9 g.) was collected. Recrystallization twice from benzenepetroleum ether gave 1.0 g. of 2-(2-chloropyrid-3-yl)oxazolo[5,4-b]pyridine, m.p. 140°–141° C.

Step C: Preparation of 2-(2-cyanopyrid-3-yl)oxazolo[5,4-]pyridine, [5,4-b]pyridine A mixture of 700 mg. of the chloro compound from Step B and 1 g. of cuprous cyanide in 30 ml. of dry N-methylpyrrolidinone was purged with nitrogen for 10 minutes, then heated in an oil bath at 175° C. for 5 hours. The cooled reaction mixture was poured into 100 ml. of ammonium hydroxide (2 parts water to 1 part of concentrated ammonia). The precipitate was collected and washed with more diluted ammonium hydroxide solution until it was colorless. The solids were extracted with boiling benzene (60 ml.) which on cooling gave 300 mg. of 2-(2-cyanopyrid-3-yl)oxazolo[5,4-b]pyridine, m.p. 129°–133° C.

EXAMPLE 249

2-Phenyl-5-Benzoylaminothiazolo[4,5-b]pyridine

A mixture of 2.0 g. of 2,6-diamino-3-mercaptopyridine and 15 g. of benzoic anhydride is heated to reflux temperature for 10 minutes. After cooling somewhat, the still liquid mixture is poured into 300 ml. of benzene. The benzene solution is extracted with 4 × 10 ml. of 6 N hydrochloric acid. The combined acid solution is then made basic with sodium hydroxide to precipitate 2-phenyl-5-benzoylaminothiazolo[4,5-b]pyridine which is recrystallized from ethanol.

Employing the procedure of Example 249 but substituting for the 2,6-diamino-3-mercaptopyridine and the benzoic anhydride employed therein, equivalent amounts of 2-amino-3-mercaptopyridine and an anhydride of formula $(R-CO)_2O$, there are produced the 2-R-thiazolo[4,5-b]pyridines described in Table IX, in accordance with the following equation:

TABLE VII $R^1_m$-[pyridine with SH and NH$_2$] + $(R-CO)_2O$ → $R^1_m$-[thiazolo[4,5-b]pyridine with S, N, R]

| Example | R¹ | R |
|---------|----|----|
| 250 | H | phenyl |
| 251 | H | 2-fluorophenyl |
| 252 | H | 2-nitrophenyl |
| 253 | H | 2-cyanophenyl |
| 254 | H | 4-fluorophenyl |
| 255 | H | 4-methoxyphenyl |
| 256 | H | 4-chlorophenyl |
| 257 | H | 2,6-difluorophenyl |
| 258 | H | 2,6-dichlorophenyl |

EXAMPLE 259

2-(2-Cyanophenyl)oxazolo[4,5b]pyridine

A mixture of 2.8 g. of 2-(2-bromophenyl)oxazolo[4,5-b]pyridine, 1.6 g. of cuprous cyanide and 15 ml. of N-methylpyrrolidinone was deairated by bubbling nitrogen through the mixture for 5 minutes. It was then heated to 175° C. in an oil-bath and held at that temperature for 5 hours under a nitrogen atmosphere and then allowed to cool to room temperature. The reaction mixture was treated with 75 ml. of 10% ammonium hydroxide and the resulting precipitate was collected. The precipitate was extracted with 100 ml. of boiling methylene chloride and the methylene chloride was evaporated. The residue was recrystallized from methylene chloride to give 2-(2-cyanophenyl)oxazolo[4,5-b]pyridine, m.p. 166°–167° C.

EXAMPLE 260

5-Cyano-2-phenyloxazolo[5,4-b]pyridine

A mixture of 2.3 g. of 5-chloro-2-phenyloxazolo[5,4-b]pyridine, 1.6 g. of cuprous cyanide and 15 ml. of N-methyl pyrrolidinone is stirred under nitrogen and then heated in an oil bath of 175° C. (bath temperature). It is maintained at that temperature for 5 hours. The cooled, dark mixture is diluted with 75 ml. of 10% ammonium hydroxide and a dark precipitate removed by filtration. The solid is extracted with methylene dichloride. The methylene dichloride is evaporated and the residue crystallized from ethyl acetate.

EXAMPLE 261

2-(4-Carboxyphenyl)oxazolo[5,4-b]pyridine

To 10 ml. of concentrated sulfuric acid at room temperature is added 2.2 g. of 2-(4-cyanophenyl)oxazolo[5,4-b]pyridine with stirring. After 2.5 hours, 0.75 g. of finely divided sodium nitrite is slowly added and then stirred overnight. After warming on the steam bath for 30 minutes it is poured onto ice. The precipitated product is recrystallized from methanol to give 2-(4-carboxyphenyl)oxazolo[5,4-b]pyridine.

EXAMPLE 262

2-(4-Cyanomethylphenyl)oxazolo[5,4-b]pyridine

Ten grams of 4-(cyanomethyl)benzoic acid is refluxed in 70 mls. of thionyl chloride for four hours. The solvents are removed leaving a residue of 4-cyanomethylbenzoyl chloride. To a solution of 5.5 g. of 3-amino-2-hydroxy pyridine in cold pyridine there is added slowly, with cooling, 8 g. of 4-cyanomethyl benzoyl chloride. The mixture is allowed to come to room temperature and stirred overnight. The mixture is added to 300 ml. of ice and the solid amide separated by filtration and recrystallized from methanol. A mixture of 3 g. of the above amide in 50 mls. of phosphorus oxychloride is heated under reflux for 5 hours. The solvents are removed in vacuo and the residue is crystallized from ethyl acetate to give 2-(4-cyanomethylphenyl)oxazolo[5,4-b]pyridine.

EXAMPLE 263

2-(4-Carboxymethylphenyl)oxazolo[5,4-b]pyridine

To 4 ml. of concentrated sulfuric acid at room temperature is added 1 g. of 2-(4-cyanomethylphenyl)oxazolo[5,4-b]pyridine. After stirring for 2 hours, 0.4 g. of powdered sodium nitrite is added. After stirring overnight the mixture is warmed in the steam bath for 30 minutes and poured onto ice. The precipitated product is crystallized from methanol to give 2-(4-carboxymethylphenyl)oxazolo-[5,4-b]pyridine.

EXAMPLE 264

2-[3-(Aminomethyl)phenyl]oxazolo[4,5-b]pyridine

A mixture of 2-(3-cyanophenyl)oxazolo[4,5-b]-pyridine (2.2 g., 0.01 m.), 200 ml. of glacial acetic acid and 1.0 g. of PtO$_2$ catalyst is reacted in a 40 p.s.i. hydrogen atmosphere at room temperature until the theoretical amount of hydrogen has been absorbed. The mixture is filtered, the acetic acid removed in vacuo to yield 2-[3-(aminomethyl)phenyl]oxazolo[4,5-b]pyridine.

EXAMPLE 265

2-[3-(Dimethylaminomethyl)phenyl]oxazolo[4,5-b]pyridine

Employing the procedure substantially as described in Example 60, but substituting for the 2-(3-nitrophenyl)oxazolo[4,5-b]pyridine used therein, an equal amount of 2-[3-(aminomethyl)phenyl]oxazolo[4,5-b]pyridine, there is produced 2-[3-(dimethylaminomethyl)phenyl]oxazolo[4,5-b]pyridine.

EXAMPLE 266

2-[3-(Methylamino)phenyl]oxazolo[4,5-b]pyridine

To a suspension of 1.2 g. (0.006 mole) of 2-(3-aminophenyl)oxazolo[4,5-b]pyridine 15 ml. of ethanol is added 0.9 g. (0.006 mole) of phthalimide followed by 0.6 ml. of 37% formaldehyde solution. The suspension is then heated on the steam cone, during which time a solution occurs followed by precipitation of a new solid. After heating for 3 hours, the mixture is cooled, filtered, the product washed one time with ethanol and dried to give 1.6 g. of 2-[3-(phthalimidomethylamino)phenyl]oxazolo[4,5-b]pyridine, m.p. 220.5°–222.5° C. after recrystallization from ethylacetate.

The phthalimido compound is then reduced with hydrogen (1100 p.s.i.) in 50 ml. of ethanol using a Raney nickel catalyst (0.3 g.), at 80° C. for 3 hours. The cooled mixture is filtered, the cake washed well with ethanol, the ethanol removed, and the residue is treated with dilute hydrochloric acid. The acid mixture is filtered, made alkaline with sodium bicarbonate and the precipitate is collected. The crude product is taken up in methylene chloride and treated with ethereal hydrogen chloride. The precipitated hydrochloride of 2-[3-(methylamino)phenyl]oxazolo[4,5-b]pyridine is collected.

EXAMPLE 267

2-(3-Mercaptophenyl)oxazolo[4,5-b]pyridine

In a 1 l. flask, equipped with a mechanical stirrer and thermometer for reading low temperatures, and immersed in an ice bath, are placed 150 ml. of concentrated hydrochloric acid and 150 g. of crushed ice. The stirrer is started, and 15.8 g. (0.075 mole) of 2-(3-aminophenyl)oxazolo[4,5-b]pyridine is slowly added. The mixture is cooled to 0° C., and a cold solution of 5.5 g (0.08 mole) of sodium nitrate in 12.5 ml. of water is slowly added, the temperature being kept below 4° C.

In a flask equipped with a thermometer, dropping funnel, and stirrer is placed a solution of 14.0 g. of potassium ethyl xanthate in 18.0 ml. of water. This mixture is warmed to 40°–45° C. and kept in that range during the slow addition of the cold diazonium solution. After an additional 30 minutes at this temperature the ethyl xanthate intermediate is separated and the aqueous layer is extracted twice, using 10.0 ml. portions of ether. The combined ethyl xanthate intermediate and extracts are washed once with 10.0 ml. of 10% sodium hydroxide solution and then with several portions of water until the washings are neutral to litmus. The ether solution is dried over anhydrous calcium chloride, and the ether is removed by distillation. The crude residual ethyl xanthate intermediate is dissolved in 50.0 ml. of 95% ethanol, the solution brought to boiling, and the source of heat removed. To this hot solution is added slowly 17.5 g. of potassium hydroxide pellets so that the solution keeps boiling, and the mixture is refluxed 8 hours. Approximately 40.0 ml. of ethanol is then removed by distillation on a steam bath, and the residue is taken up in the minimum of water. The aqueous solution is extracted with three 10.0 ml. portions of ether, the extract being discarded. The aqueous solution is adjusted to near neutrality using 6 N sulfuric acid. The precipitate is collected and recrystallized from ethyl acetate to give 2-(3-mercaptophenyl)oxazolo[4,5-b]pyridine.

EXAMPLE 268

2-[3-(2-Dimethylaminoethoxy)phenyl]oxazolo[4,5-]pyridine

To a solution of 1.1 g. (0.005 mole) of 2-(3-hydroxyphenyl)oxazolo[4,5-b]pyridine in 15 ml. dried dimethylformamide is added 0.6 g. (0.011 mole) of sodium methoxide in portions over about 10 min. To the reddish-orange solution cooled in an ice-bath is added 0.72 g. (0.005 mole) of N,N-dimethyl-2-chloroethylamine hydrochloride in portions over 15 minutes. The resultant mixture is then stirred 10 minutes, set in an oil-bath at 75° C., and kept at 75°–90° C. (bath) for 20 hours. After cooling to room temperature, 15 ml. of dried ether is added with stirring, and the resultant mixture is filtered. The filtrate is then stripped of solvent, and the residue distributed between methylene chloride and water. The organic layer is dried over sodium sulfate, filtered, and concentrated in vacuo to yield 2-[3-(2-dimethylaminoethoxy)phenyl]oxazolo[4,5-b]pyridine.

EXAMPLE 269

2-[3-(2-Dimethylaminoethyl)aminophenyl]oxazolo[4,5-b]pyridine

A mixture of 1.1 g., (0.005 mole) of 2-(3-aminophenyl)oxazolo[4,5-b]pyridine and 50 ml. of ethanol is reacted with dimethylaminoacetaldehye [from 0.96 g. (0.006 mole) dimethylaminoacetaldehyde diethylacetal]by gentle heating to complete the intermediate Schiff base formation. The mixture is then cooled and 60 mg., (0.0015 mole) of sodium borohydride is added, and the mixture allowed to stir overnight at room temperature. Water is added, the solvents are removed in vacuo, and the residue is distributed between water and methylene chloride. The organic layer is dried and concentrated in vacuo to give crude 2-[3-(2-dimethylaminoethyl)aminophenyl]oxazolo[4,5-b]pyridine, purified via column chromatography using an alumina column with an ethylacetate-ether mixture (v/v 0–60% ethylacetate) as eluant.

The compound is also obtained via direct alkylation of starting amine using 2-dimethylaminoethyl chloride hydrochloride and base in the usual manner.

EXAMPLE 270

2-(2-methyl-3-chlorophenyl)oxazolo[4,5-b]pyridine

A mixture of 3.4 g. of 2-methyl-3-chlorobenzoic acid and 1.0 g. of 2-amino-3-hydroxypyridine was ground in a mortar and intimately mixed with 17 g. of polyphosphoric acid. The gummy mixture, under nitrogen, was slowly heated over 75 minutes to 178° C. with stirring. The resulting solution was poured slowly into 300 ml. of ice-water with stirring. After 1 hour the precipitate was collected and added with stirring to dilute sodium hydroxide solution. After 15 minutes the precipitate was collected, washed with water and dried to give 2.1 g. of crude product. This was recrystallized by dissolving in 75 ml. of cyclohexane, filtering, concentrating to about 50 ml., and cooling to give 1.76 g. of 2-(2-methyl-3-chlorophenyl)oxazolo[4,5-b]pyridine, m.p. 118.5°-120° C.

Employing the procedure substantially as described in Example 270, but substituting for the 2-methyl-3-chlorobenzoic acid used therein an equimolar amount of 2-chloro-3-methylbenzoic acid, there is produced 2-(2-chloro-3-methylphenyl)oxazolo[4,5-b]pyridine, m.p. 75°-77° C.

EXAMPLE 271

2-(3,5-dimethylphenyl)oxazolo[4,5-b]pyridine

To a swirled mixture of 5.5 g. of 2-amino-3-hydroxypyridine and 12.0 g. of 3,5-dimethylbenzoic acid was added 30 g. of polyphosphoric acid. The mixture was heated slowly with stirring and under nitrogen to 170°-180° C. After 15 minutes at this temperature, the mixture was added to 500 ml. of ice-water and basified with sodium bicarbonate, followed by ammonium hydroxide to maintain pH 8-10. After 1 hour of stirring the precipitate was collected on a filter and washed thoroughly with water and air dried to give 11.0 g. of crude product, m.p. 148°-152° C. The crude material was dissolved in 200 ml. of warm benzene, filtered through about 40 ml. of aluminum oxide powder and concentrated to about 100 ml. While still warm, 125 ml. of petroleum ether was added. After cooling, the precipitate was collected and air dried to give 6.8 g. of 2-(3,5-dimethylphenyl)oxazolo[4,5-b]pyridine, m.p. 155°-157° C.

EXAMPLE 272

2-(2-bromo-5-aminophenyl)oxazolo[4,5-b]pyridine

A solution of 3.5 g. of 2-(2-bromo-5-nitrophenyl)oxazolo[4,5-b]pyridine (from Example 6 (g)) in 75 ml. of methanol and 2 ml. of glacial acetic acid was hydrogenated with ⅛ teaspoon of Raney nickel catalyst, at room temperature under 40 p.s.i.g. (3.7 atmospheres). The catalyst was removed by filtration, and the filtrate was evaporated to dryness. The residue was dissolved in 200 ml. hot benzene, concentrated to about 25 ml., and cooled. The precipitate was collected and air dried to give 0.9 g. of 2-(2-bromo-5-aminophenyl)oxazolo[4,5-b]pyridine, m.p. 172°-174° C.

EXAMPLE 273

2-(3-isopropoxyphenyl)oxazolo[4,5-b]pyridine 2-(3-Hydroxyphenyl)oxazolo[4,5-b]pyridine (1 g.) was added to an ice cold stirred mixture of 208 mg. of sodium hydride and 5 ml. of dry dimethylformamide under nitrogen. After 5 minutes 0.49 ml. of isopropyl bromide was added and stirring was continued at 0° C. for 1 hour. After 5 hours at room temperature 0.5 ml. of isopropyl bromide was added and stirring was continued for 5 days. The solvent was evaporated at 20°-50° in vacuo. The residue was dissolved in 20 ml. of warm benzene, treated with decolorizing charcoal and filtered. The filtrate was concentrated to 0.98 g. of oil. The oil was extracted with 40 ml. of hot cyclohexane, and the extract was washed with potassium carbonate solution, dried over potassium carbonate and concentrated to 0.9 g. solid. The solid was extracted with n-hexane. Cooling the extract gave 0.42 g. of 2-(3-isopropoxyphenyl)oxazolo[4,5-b]pyridine, m.p. 68.5°-70.5° C.

EXAMPLE 274

2-(3-Chloro-2,5-dimethylphenyl)oxazolo[4,5-b]pyridine

Step A: Preparation of 3-amino-2,5-dimethylbenzoic acid 2,5-Dimethyl-3-nitrobenzoic acid (10.0 g.) was hydrogenated in 200 ml. of methanol in the presence of 0.5 g. of 5% palladium on carbon. The catalyst was removed on a filter and the filtrate was concentrated to dryness to give 8.3 g. of 3-amino-2,4-dimethylbenzoic acid, m.p. 145.5°-146.5° C.

Step B: Preparation of 3-chloro-2,5-dimethylbenzoic acid

A slurry of 4.95 g. of amino compound from Step A in 25 ml. of 6 N hydrochloric acid was cooled in an ice-acetone bath (−3° to 0° C.) and a solution of 2.3 g. of sodium nitrite in 6 ml. of water was added in 0.5 ml. portions over about 20 minutes. After about 1 hour at 0-5° C., the mixture was poured into a solution of 4 g. of cuprous chloride in 25 ml. of concentrated hydrochloric acid at 1° C. After 0.5 at 1°-2° C., 2 hours at room temperature, 1 hour at 60° C. and 15 hours at room temperature, the precipitate was collected, washed with water, and dried to give 4.5 g. of 3-chloro-2,5-dimethylbenzoic acid, m.p. 167.5°-170° C.

Step C: Preparation of 2-(3-chloro-2,5-dimethylphenyl)oxazolo[4,5-b]pyridine

Follwing the procedure substantially as described in Example 1; but substituting for the 2-methyl-3-chlorobenzoic acid used therein, a molar equivalent of 3-chloro-2,5-dimethylbenzoic acid, there is produced 2-(3-chloro-2,5-dimethylphenyl)oxazolo[4,5-b]pyridine, m.p. 99.5°-101° C.

EXAMPLE 275

2-(2-Chloro-5-t-butylphenyl)oxazolo[4,5-b]pyridine

Step A: Preparation of 5-t-butyl-2-nitrobenzoic acid 3-t-Butylbenzoic acid (7.0 g.) was added portionwise over 50 minutes to 50 mml. of fuming red nitric acid at −5° C. with stirring. After 15 minutes at 0° C., the mixture was poured into ice-water and after stirring for 15 minutes the precipitate was collected and washed with water (m.p. 128°-134° C.). This (12 g.) was dissolved in 65 ml. of ethanol, filtered, heated to 70° C. and water added to about 400 ml. volume. After cooling, the precipitate was collected, washed with water, and dried (9.55 g.). This was extracted with 200 ml. of warm cyclohexane and the insoluble material was collected to give 6.4 g. 5-t-butyl-2-nitrobenzoic acid, m.p. 137°-139° C.

Step B: Preparation of 2-amino-5-t-butylbenzoic acid

The nitro compound from Step A (6.2 g.) was hydrogenated in 100 ml. of methanol over 0.5 g. of 5% palladium on carbon. The catalyst was removed on a filter, and the filtrate was concentrated to dryness to give 5.0 g. of 2-amino-5-t-butylbenzoic acid, m.p. 142°–145° C. resolidifying and remelting at 151° C.

Step C: Preparation of 2-chloro-5-t-butylbenzoic acid

The amino compound (3.86 g.) from Step B was stirred in 25 ml. of 6 N hydrochloric acid and at −2° C. a solution of 1.6 g. of sodium nitrite in 3 ml. of water was added over 0.5 hour. After an additional 0.5 hour at 0° C. the mixture was poured into 2.7 g. of cuprous chloride in 20 ml. of concentrated hydrochloric acid at 0° C. After 0.5 hour at 0° C. and 0.5 hour at room temperature, the precipitate was collected, washed with water and dried to give A (0.17 g., m.p. 88°–94° C.). The filtrate plus a little copper powder was heated at 100° C. for 0.5 hour and cooled. The precipitate was collected, dissolved in sodium hydroxide and reprecipitated by adding hydrochloric acid. This material was collected, washed with water and dried to give B (3.15 g., m.p. 99°–103° C.). A and B were combined and recrystallized from 20 ml. of n-hexane to give 1.6 g. of 2-chloro-5-t-butylbenzoic acid, m.p. 106°–108.5° C.

Step D: Preparation of 2-(2-chloro-5-t-butylphenyl)oxazolo[4,5-b]pyridine

Employing the procedure substantially as described in Example 1, but substituting for the 2-methyl-3-chlorobenzoic acid used therein a molar equivalent of 2-chloro-5-t-butylbenzoic acid, there is obtained 2-(2-chloro-5-t-butylphenyl)oxazolo[4,5-b]pyridine, m.p. 111°–112° C.

EXAMPLE 276

2-(3-t-butyl-5-methoxyphenyl)oxazolo[4,5-b]pyridine

Step A: Preparation of 3-t-butyl-5-methoxybenzoic acid

A mixture of 2.8 g. of potassium hydroxide in 9 ml. of water, 17.1 g. of pyridine and 5.0 g. of 3-t-butyl-5-methoxytoluene was heated in an oil bath at 95° C. With rapid stirring 11.1 g. of potassium permanganate was added over 2 hours and heating at 95° C. was continued for 1.5 hours more. After cooling to room temperature 5 ml. of alcohol was added. The mixture was filtered and the filtrate was shaken with 100 ml. ether to give 3 layers. The bottom layer (50 ml.) and middle layer (25 ml.) were collected separately, each was concentrated to about ½ volume, and acidified to pH 2 with 4N sulfuric acid. The precipitates were collected, washed with water, and air dried to give respectively 0.6 g. and 1.1 g. of crude product, m.p. 75°–85° C. which, after combining and recrystallizing from 10 ml. of acetic acid and 5 ml. of water, gave 0.85 g. of 3-t-butyl-5-methoxybenzoic acid, m.p. 84°–87° C.

Step B: Preparation of 2-(3-t-butyl-5-methoxyphenyl)oxazolo[4,5-b]pyridine

A mixture of 6.0 g. of polyphosphoric acid, 0.8 g of 3-t-butyl-5-methoxybenzoic acid, and 0.46 g. of 2-amino-3-hydroxypyridine under nitrogen was placed in a pre-heated oil bath at 150° C. After about 12 minutes of stirring, the melt was poured into 100 ml. of an ice slurry. The precipitated gum was taken up in methylene chloride, washed with 1 × 20 ml. of 2.5 N sodium hydroxide and 1 × 25 ml. of water, dried over magnesium sulfate, filtered, and concentrated to oil which crystallized to give 0.8 g. of product, which after recrystallization from n-hexane gave 0.5 g. of 2-(3-t-butyl-5-methoxyphenyl)oxazolo[4,5-b]pyridine, m.p. 119°–121° C.

EXAMPLE 277

A mixture of 250 parts of 2-(2-fluorophenyl)oxazolo[4,5-b]pyridine and 25 parts of lactose is granulated with suitable water, and to this is added 100 parts of maize starch. The mass is passed through a 16 mesh screen. The granules are dried at a temperature below 60° C. The dry granules are passed through a 16 mesh screen, and mixed with 3.8 parts of magnesium stearate. They are then compressed into tablets suitable for oral administration.

The specific oxazolopyridine used in the foregoing example may be replaced by 25, 100, 250, or 500 parts of other oxazolopyridines or thiazolopyridines of this invention to produce tablets suitable for oral administration as an antiinflammatory, antipyretic, and/or analgesic according to the method of this invention.

EXAMPLE 278

A mixture of 50 parts of 2-(2,6-difluorophenyl)oxazolo[5,4b]pyridine, 3 parts of the calcium salt of lignin sulphonic acid, and 237 parts of water is ballmilled until the size of substantially all of the particles is less than 10 microns. The suspension is diluted with a solution containing 3 parts of sodium carboxymethylcellulose and 0.9 parts of the butyl ester of p-hydroxybenzoic acid in 300 parts of water. There is thus obtained an aqueous suspension suitable for oral administration for therapeutic purposes.

EXAMPLE 279

A mixture of 250 parts of 2-(2-fluorophenyl)oxazolo[5,4-]pyridine, 200 parts of maize starch and 30 parts of alginic acid is mixed with a sufficient quantity of 10% aqueous paste of maize starch, and granulated. The granules are dried in a current of warm air and the dry granules are then passed through a 16-mesh screen, mixed with 6 parts of magnesium stearate and compressed into tablet form to obtain tablets suitable for oral administration.

EXAMPLE 280

A mixture of 500 parts 2-phenyloxazolo[5,4-b]pyridine, 60 parts maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into tablet form suitable for oral administration.

EXAMPLE 281

1. Tablets 10,000 scored tablets for oral use, each containing 500 mg. of active ingredient are prepared from the following ingredients:

|  | Gm. |
|---|---|
| 2-(2-nitrophenyl)oxazolo[5,4-b]pyridine | 5000 |
| Starch, U.S.P. | 350 |
| Talc, U.S.P. | 250 |
| Calcium stearate | 35 |

The powdered oxazolopyridine is granulated with a 4% w./v. aqueous solution of methylcellulose U.S.P. (1500 cps.). To the dried granules is added a mixture of the remainder of the ingredients and the final mixture compressed into tablets of proper weight.

2. Capsules 10,000 two-piece hard gelatine capsules for oral use, each containing 250 mg. of oxazolopyridine are prepared from the following ingredients:

|  | Gm. |
|---|---|
| 2-(2,6-difluorophenyl)oxazolo-[4,5-b]pyridine | 2500 |
| Lactose, U.S.P. | 1000 |
| Starch, U.S.P. | 300 |
| Talc, U.S.P. | 65 |
| Calcium stearate | 25 |

The powdered oxazolopyridine is mixed with the starch-lactose mixture followed by the talc and calcium stearate. The final mixture is then encapsulated in the usual manner. Capsules containing 10, 25, 50 and 100 mg. of oxazolopyridine are also prepared by substituting 100, 250, 500 and 1000 gm. of 2500 gm. in the above formulation.

3. Soft Elastic Capsules

One-piece soft elastic capsules for oral use, each containing 200 mg. of oxazolopyridine are prepared in the usual manner by first dispersing the powdered active material in sufficient corn oil to render the material capsulatable.

4. Aqueous suspension

A aqueous suspension for oral use containing in each 5 ml., 1 gram of oxazolopyridine is prepared from the following ingredients:

|  | Gm. |
|---|---|
| 2-(2-fluorophenyl)oxazolo[4,5-b]-pyridine | 2000 |
| Methylparaben, U.S.P. | 7.5 |
| Propylparaben, U.S.P. | 2.5 |
| Saccharin sodium | 12.5 |
| Glycerin | 3000 |
| Tragacanth powder | 10 |
| Orange oil flavor | 10 |
| F.D. & C. orange dye | 7.5 |
| Deionized water, q.s. to 10,000 mg. | |

EXAMPLE 282

Gel Formulation
0.1 mg. disodium edetate
1.30 mg. of purified H$_2$O
300 mg. isopropanol
26 mg. hydroxypropylcellulose
q.s.a.d. 1 gm. propylene glycol
1.09 mg. 2-(2-methyl-3--chlorophenyl)oxazolo[4,5-b]pyridine

EXAMPLE 283

Ointment Formulation
50 mg. wool alcohols B.P.
150 mg. amichol C
350 mg. wax white Be square 170°/175° C. q.s.a.d. 1 gm. isopropyl myristate
1.09 mg. 2-(2-chloro-3-methylpheny)oxazolo[4,5-b]-pyridine
0.4% citric acid anhydrous '58% sodium phosphate disbasic anhydrous.

EXAMPLE 284

2-[3,5-di(t-butyl)phenyl]oxazolo[4,5-b]pyridine

A mixture of 30 g. of polyphosphoric acid, 5.0 g. of 3,5-di(t-butyl)benzoic acid and 2.1 g. of 2-amino-3-hydroxypyridine, under nitrogen and with rapid stirring, was heated at 180° C. for 40 minutes. The mixture was poured into 500 ml. of an ice-water mixture. The mixture was adjusted to pH 8.0 with concentrated ammonium hydroxide and stirred until the precipitate was finely divided. The precipitate was collected on a filter, washed with 2 × 100 ml. of water, and dried. The crude product was dissolved in 200 ml. of n-hexane, treated with decolorizing carbon, filtered and concentrated to about 75 ml. On cooling, the product crystallized to give 3.5 g . of 2-[3,5-di(t-butyl)phenyl]oxazolo[4,5-b]pyridine, m.p. 154°–156° C.

EXAMPLE 285

2-[3,5-Di(isobutyl)phenyl]oxazolo[4,5-b]pyridine

Step A: Preparation of 2[3,5-di(bromomethyl)phenyl]oxazolo[4,5-b]pyridine

A mixture of 10 mmoles of 2-(3,5-dimethylphenyl)oxazolo[4,5-b]pyridine and 21 mmoles of N-bromosuccinimide in 50 ml. of carbon tetrachloride is stirred and irradiated with a sun lamp for 45 minutes. The insolubles are removed by filtration and the filtrate is concentrated to dryness with a stream of nitrogen and the residue is triturated with 25 ml. of methanol. The crude 2-[3,5-di(bromomethyl)phenyl]oxazolo[4,5-b]pyridine is collected.

Step B: Preparation of 2-[3,5-di(2-methylallyl)phenyl]oxazolo[4,5b]pyridine

A mixture of 5 mmoles of the product from Step A and 11.0 mmoles of triphenylphosphine in 15 ml. of dimethylformamide is stirred and refluxed under nitrogen for 3 hours. The mixture is cooled and the phosphonium salt is collected on a filter. A mixture of 4 mmoles of the phosphonium salt, 100 ml. of ethanol, 1 ml. of acetone and 40 ml. of 0.3 N ethanolic lithium ethoxide is stirred at room temperature under nitrogen for 2 hours. Water (100 ml.) is added and the mixture is cooled in an ice-bath. The precipitate is collected and purified by chromatography on silica gel using 2% methanol in chloroform as the eluant to give 2-[3,5-di(2-methylallyl)phenyl]oxazolo[4,5-b]pyridine.

Step C: Preparation of 2-[3,5-di(isobutyl)phenyl]oxazolo[4,5-b]pyridine

The product from Step B (3 mmoles) is hydrogenated in 25 ml. of methanol in the presence of 500 mg. of 5% palladium on carbon under 3 atmospheres of hydrogen. The catalyst is removed by filtration and the filtrate is concentrated to dryness. The residue is recrystallized from n-hexane to give 2-[3,5di(isobutyl)phenyl]oxazolo[4,5-b]pyridine.

EXAMPLE 286

2-(3-t-Butyl-2-methoxyphenyl)oxazolo[4,5-b]pyridine

Step A: Preparation of 3-t-butyl-2-methoxytoluene

A mixture of 0.12 mole of 2-t-butyl-6-methylphenol and 12.0 ml. of 10.0 N sodium hydroxide solution is stirred and heated on the steam bath for 1 hour. The water is evaporated in vacuo. The residue is added portion-wise with stirring to 0.24 mole of dimethylsulfate and the mixture is stirred at 95° C. for 6 hours and at room temperature for 15 hours. Sodium carbonate (0.25 mole) in 100 ml. of water is added and stirring is continued for 5 hours. The mixture is extracted with 3 × 100 ml. of ether and the extract is dried and concentrated to dryness to give 3-t-butyl-2-methoxytoluene.

Step B: Preparation of 3-t-butyl-2-methoxybenzoic acid

A mixture of 0.01 mole of 3-t-butyl-2-methoxytoluene, 0.01 mole of potassium permanganate, and 100 ml. of 1 N sodium hydroxide solution is heated to reflux and another 0.01 mole of potassium permanganate is added each hour until a total of 0.05 mole has been added (4 hours). After another 2 hours of reflux the unreacted starting material is steam distilled. Ethanol is added to the residue to decompose excess permanganate and mixture is filtered hot. Acidification with sulfuric acid of the filtrate causes precipitation of the product which is collected, washed with water and dried to give 3-t-butyl-2-methoxybenzoic acid.

Step C: Preparation of 2-(3-t-butyl-2-methoxyphenyl)oxazolo[4,5-b[pyridine

Employing the procedure of Example 6 but substituting for the 2-fluorobenzoic acid used therein an equivalent amount of 3-t-butyl-2-methoxybenzoic acid, there is produced 2-(3-t-butyl-2-methoxyphenyl)oxazolo[4,5-b]pyridine.

What is claim is:

1. A compound of structural formula:

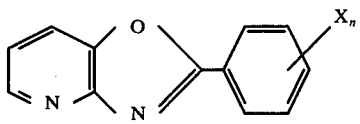

wherein $n$ is an integer from 1 to 2 and X is the same or different and is halo, lower alkyl, trifluoromethyl, lower alkoxy, nitro or cyano.

2. 2-(2-Fluorophenyl)oxazolo[4,5-]pyridine.
3. 2-(2-Cyanophenyl)oxazolo[4,5-b]pyridine.
4. 2-(2,6-Difluorophenyl)oxazolo[4,5-b]pyridine.
5. 2-(3Methoxyphenyl)oxazolo[4,5]pyridine.
6. 2-(3,5-Dimethylphenyl)oxazolo[4,5-b]pyridine.
7. 2(2-Methyl-3-chlorophenyl)oxazolo[4,5b]pyridine.
8. 2-(2-Chloro-3-methylphenyl)oxazolo[4,5-b]pyridine.
9. 2-(2-Methyl-3-methoxphenyl)oxazolo[4,5-b]-pyridine.
10. 2-[3,5-di(t-butyl)phenyl)oxazolo[4,5-b]pyridine.
11. 2-(3-t-Butylphenyl)oxazolo[4,5-b]pyridine.
12. 2-(3-t-Butyl-5-methylphenyl)oxazolo[4,5b]pyridine.
13. 2-(3-t-Butyl-5-methoxyphenyl)oxazolo[4,5-b]pyridine.
14. A method of treating inflammation, fever or pain in warm-blooded animals and humans in need of such treatment which comprises administration of an effective amount of a compound of structural formula:

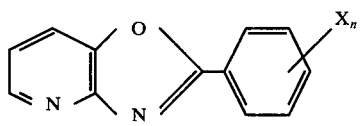

wherein $n$ is an integer from 1 to 2 and X is the same or different and is halo, lower alkyl, trifluoromethyl, lower alkoxy, nitro or cyano.

15. A method for the treatment of inflammation, fever or pain in warm-blooded animals and humans in need of such treatment which comprises systemic administration of an effective amount of a compound of structural formula:

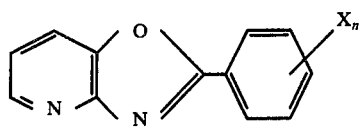

wherein $n$ is an integer from 1 to 2 and X is the same or different and is fluoro, nitro or cyano.

16. A method for the treatment of the inflammation of dermatoses in warm-blooded animals and humans in need of such treatment which comprises topical administration of an effective amount of a compound of structural formula:

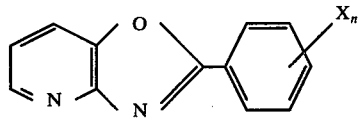

wherein $n$ is an integer from 1 to 2 and X is the same or different and is chloro, lower alkyl, trifluoromethyl or lower alkoxy.

17. The method of treatment of claim 14 which comprises administration of an effective amount of 2-(2-fluorophenyl)oxazolo[4,5-b]pyridine.
18. The method of treatment of claim 14 which comprises administration of an effective amount of 2-(2-cyanophenyl)oxazolo[4,5-b]pyridine.
19. The method of treatment of claim 14 which comprises administration of an effective amount of 2-(2,6-difluorophenyl)oxazolo[4,5-b]pyridine.
20. The method of treatment of claim 14 which comprises administration of an effective amount of 2-(3-methoxyphenyl)oxazolo[4,5-b]pyridine.
21. The method of treatment of claim 14 which comprises administration of an effective amount of 2-(3,5-dimethylphenyl)oxazolo[4,5-b]pyridine.
22. The method of treatment of claim 14 which comprises administration of an effective amount of 2-(2-methyl-3-chlorophenyl)oxazolo[4,5-b]pyridine.
23. The method of treatment of claim 14 which comprises administration of an effective amount of 2-(2-chloro-3-methylphenyl)oxazolo[4,5-b]pyridine.
24. The method of claim 15 wherein the compound is 2-(2-cyanophenyl)oxazolo[4,5-b]pyridine.
25. The method of claim 16 wherein the compound is 2-(3-methoxyphenyl)oxazolo[4,5-b]pyridine.
26. The method of claim 16 wherein the compound is 2-(3,5-dimethylphenyl)oxazolo[4,5-b]pyridine.
27. The method of claim 16 wherein the compound is 2-(2-methyl-3-chlorophenyl)oxazolo[4,5-b]pyridine.
28. The method of claim 16 wherein the compound is 2-(2-chloro-3-methylphenyl)oxazolo[4,5b]pyridine.
29. A pharmaceutical composition for systemic administration in the treatment of inflammation, fever or pain in warm-blooded animals and humans in need of such treatment comprising an inert carrier and an effective amount of a compound of structural formula

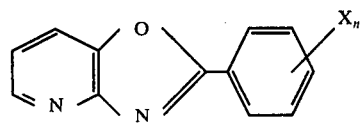

wherein *n* is an integer from 1 to 2 and X is the same or different and is fluoro, nitro or cyano.

30. A pharamaceutical composition suitable for topical administration in the treatment of the inflammation of dermatoses in warm-blooded animals and humans in need of such treatment comprising an inert carrier and an effective amount of a compound of structural formula:

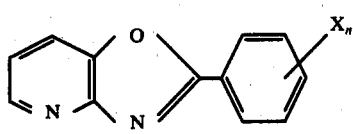

wherein *n* is an integer from 1 to 2 and X is the same or different and is chloro, lower alkyl, trifluoromethyl, or lower alkoxy.

31. The pharmaceutical composition of claim 29, wherein the compound is 2-(2-cyanophenyl)oxazolo[4,5-b]pyridine.

32. The pharmaceutical composition of claim 29, wherein the compound is 2-(2-nitrophenyl)oxazolo[4,5-b]pyridine.

33. The composition of claim 30, wherein the compound is 2-(3-methoxyphenyl)oxazolo[4,5-b]pyridine.

34. The composition of claim 30, wherein the compound is 2-(3,5-dimethylphenyl)oxazolo[4,5-b]pyridine.

35. The composition of claim 30, wherein the compound is 2-(2-methyl-3-chlorophenyl)oxazolo[4,5-b]pyridine.

36. The composition of claim 30, wherein the compound is 2-(2-chloro-3-methylphenyl)oxazolo[4,5-b]pyridine.

* * * * *